US012613238B2

(12) United States Patent
Kalluri et al.

(10) Patent No.: US 12,613,238 B2
(45) Date of Patent: Apr. 28, 2026

(54) DIAGNOSTIC AND PROGNOSTIC UTILITY OF EXOSOMES IN IMMUNOTHERAPY

(71) Applicant: BOARD OF REGENTS, THE UNIVERSITY OF TEXAS SYSTEM, Austin, TX (US)

(72) Inventors: Raghu Kalluri, Houston, TX (US); Valerie Lebleu, Houston, TX (US); Jennifer Wargo, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 810 days.

(21) Appl. No.: 17/797,660

(22) PCT Filed: Feb. 5, 2021

(86) PCT No.: PCT/US2021/016887
§ 371 (c)(1),
(2) Date: Aug. 4, 2022

(87) PCT Pub. No.: WO2021/158966
PCT Pub. Date: Aug. 12, 2021

(65) Prior Publication Data
US 2023/0054656 A1 Feb. 23, 2023

Related U.S. Application Data

(60) Provisional application No. 62/970,611, filed on Feb. 5, 2020.

(51) Int. Cl.
*G01N 33/50* (2006.01)
*G01N 33/574* (2006.01)
*G01N 33/5751* (2026.01)

(52) U.S. Cl.
CPC ..... *G01N 33/5076* (2013.01); *G01N 33/5751* (2026.01)

(58) Field of Classification Search
None
See application file for complete search history.

(56) References Cited

U.S. PATENT DOCUMENTS

| | | |
|---|---|---|
| 2017/0130271 A1 | 5/2017 | Wong |
| 2019/0179998 A9 | 6/2019 | Frenkel et al. |
| 2020/0123258 A1 | 4/2020 | Wargo et al. |
| 2020/0345648 A1 | 11/2020 | Kalluri et al. |
| 2021/0007988 A1 | 1/2021 | Kalluri et al. |
| 2021/0024936 A1 | 1/2021 | Kalluri |
| 2021/0115449 A1 | 4/2021 | Kalluri |
| 2021/0139995 A1 | 5/2021 | Kalluri |
| 2021/0186877 A1 | 6/2021 | Shpall et al. |
| 2021/0369858 A1 | 12/2021 | Kalluri et al. |
| 2021/0371825 A1 | 12/2021 | Kalluri et al. |
| 2022/0136011 A1 | 5/2022 | Kalluri |
| 2022/0137056 A1 | 5/2022 | Kalluri |
| 2022/0144926 A1 | 5/2022 | Kalluri et al. |
| 2022/0144938 A1 | 5/2022 | Kalluri |

FOREIGN PATENT DOCUMENTS

| | | |
|---|---|---|
| JP | 2017/120263 | 7/2017 |
| JP | 2018/059865 | 4/2018 |
| WO | WO 2019/094692 | 5/2019 |
| WO | WO 2020/257296 | 12/2020 |
| WO | WO 2021/113761 | 6/2021 |
| WO | WO 2021/158966 | 8/2021 |
| WO | WO 2021/195113 | 9/2021 |
| WO | WO 2022/032238 | 2/2022 |

OTHER PUBLICATIONS

Mao et al. Circulating exosomes from esophageal squamous cell carcinoma mediate the generation of B10 and PD-1high Breg cells. Cancer Science. 2019;110:2700-2710. (Year: 2019).*
Dolgin E., PD-1 Blockade Falls Short (Repeatedly) in Prostate Cancer. (Cancer Discovery, AACRJournals.org May 2023, pp. 1033 1023). (Year: 2023).*
McGrail et al. High tumor mutation burden fails to predict immune checkpoint blockade response across all cancer types. Ann Oncol. 2021, 32(5):661-672. Urology Times, Oct. 2020. (Year: 2020).*
Nyberg K., Keynote-598: Dual PD-1 and CTLA-4 Checkpoint Blockade Confers No Therapeutic Benefit Beyond PD-1 Blockade Alone in PD-L1-Positive NSCLC. ILCN, on: Jan. 28, 2021, In: Presidential Symposium, WCLC 2020 Archive. (Year: 2020).*
Broderick, JM. Response-adaptive immunotherapy approach falls short in metastatic kidney cancer. Urology Times, Oct. 30, 2020 ( Year: 2020).*

(Continued)

*Primary Examiner* — Maher M Haddad
(74) *Attorney, Agent, or Firm* — Norton Rose Fulbright US LLP

(57) ABSTRACT

The current disclosure provides for novel therapeutic methods by identifying patient populations that may be treated effectively by immunotherapies. It was found that responders of immunotherapeutic treatments have a higher amount of B-cell exosomes in their blood than non-responders. Aspects of the disclosure relate to a method of treating cancer in a subject comprising administering to the subject immune checkpoint blockade (ICB) therapy after B-cell exosomes have been detected in a biological sample from the subject.

16 Claims, 11 Drawing Sheets

(56) References Cited

OTHER PUBLICATIONS

Logozzi et al. High Levels of Exosomes Expressing CD63 and Caveolin1 in Plasma of Melanoma PatientsPLoS ONE 4(4): e5219, 2009 (Year: 2009).*

Tucci et al. Serum exosomes as predictors of clinical response to ipilimumab in metastatic melanoma. OncoImmunology, 7:2, e1387706, 2018 (Year: 2018).*

Callahan et al. Peripheral blood and tumor biomarkers in patients with advanced melanoma treated with combination nivolumab (anti-PD-1, BMS-936558, ONO-4538) and ipilimumab. Journal for ImmunoTherapy of Cancer 2013, 1(Suppl 1):O6 (Year: 2013).*

Aheget et al., "Exosomes: Their Role In Pathogenesis, Diagnosis, and Treatment of Diseases" Cancers 2021, 13(84), 45 pages.

Helmink et al., "B cells and tertiary lymphoid structures promote immunotherapy response" Nature 2020, 577, 549-555.

International Search Report and Written Opinion issued in Corresponding PCT Application no. PCT/US2021/016887, dated May 7, 2021.

* cited by examiner

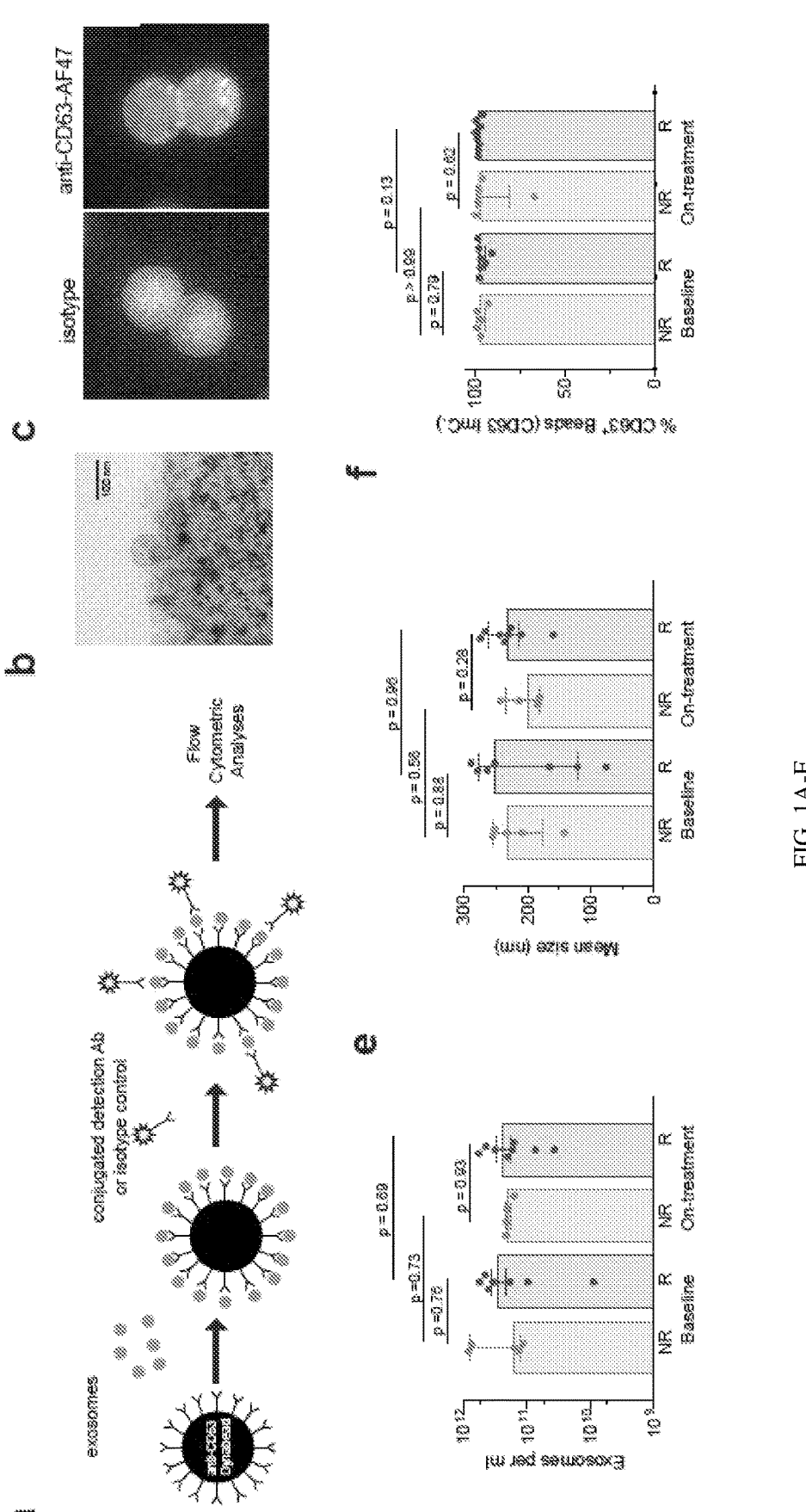
FIG. 1A-F

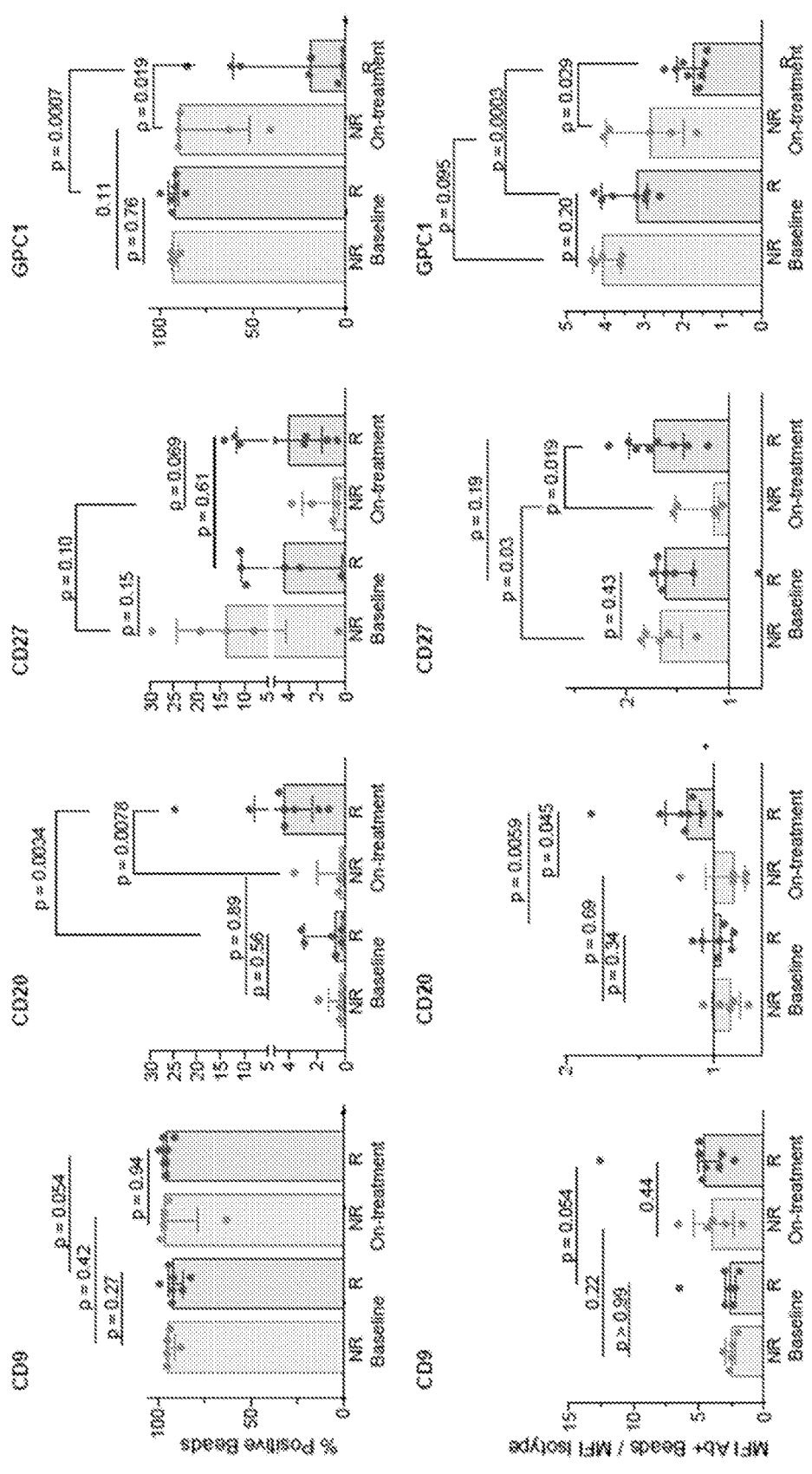
FIG. 1G-H

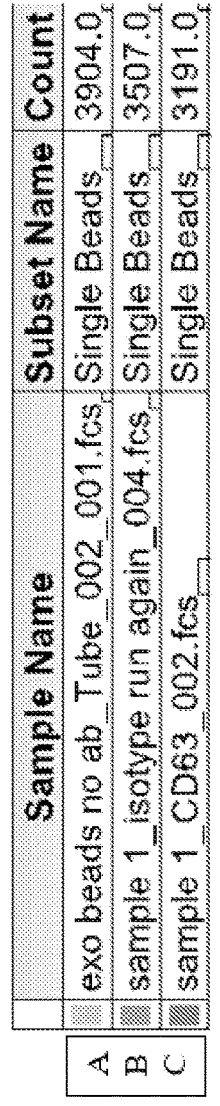
| | Sample Name | Subset Name | Count |
|---|---|---|---|
| A | exo beads no ab_Tube_002_001.fcs_ | Single Beads_ | 3904.0_ |
| B | sample 1_isotype run again_004.fcs_ | Single Beads_ | 3507.0_ |
| C | sample 1_CD63_002.fcs_ | Single Beads_ | 3191.0_ |
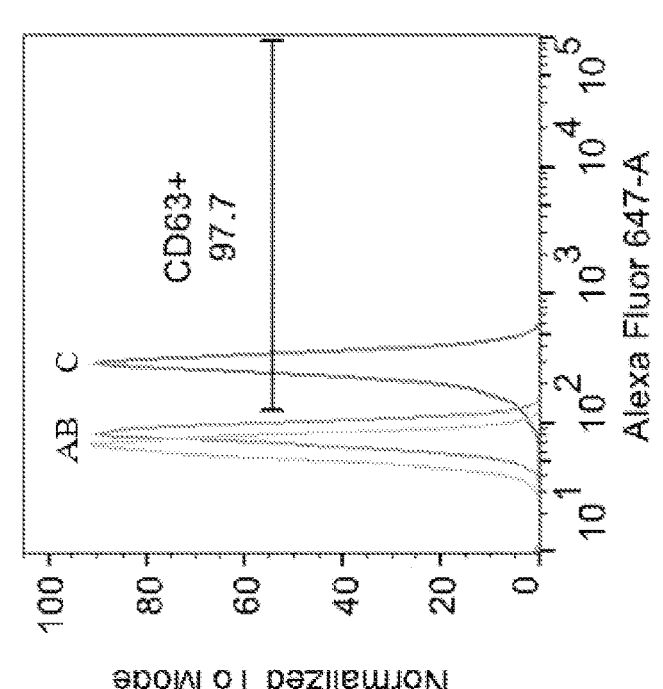
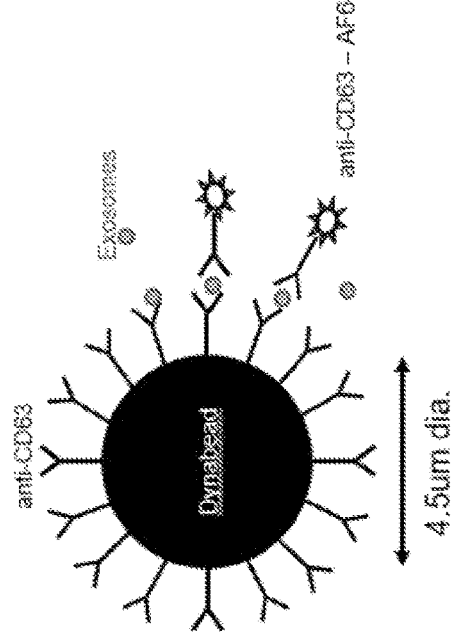
FIG. 3

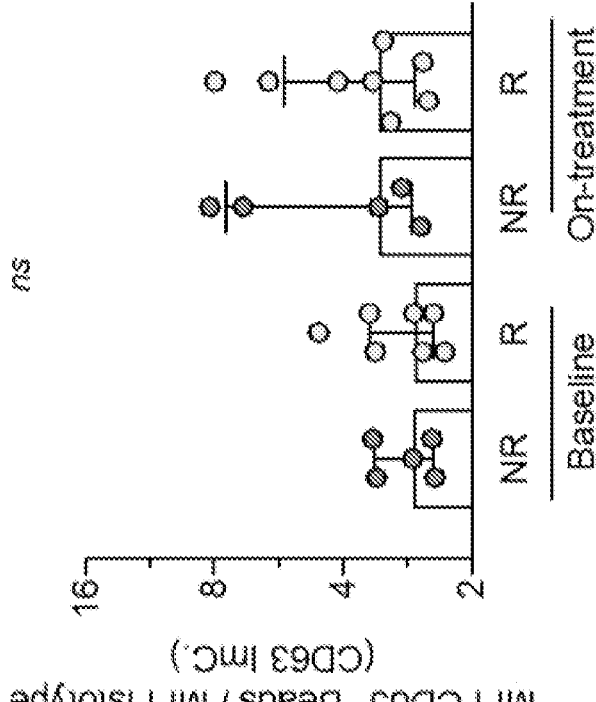
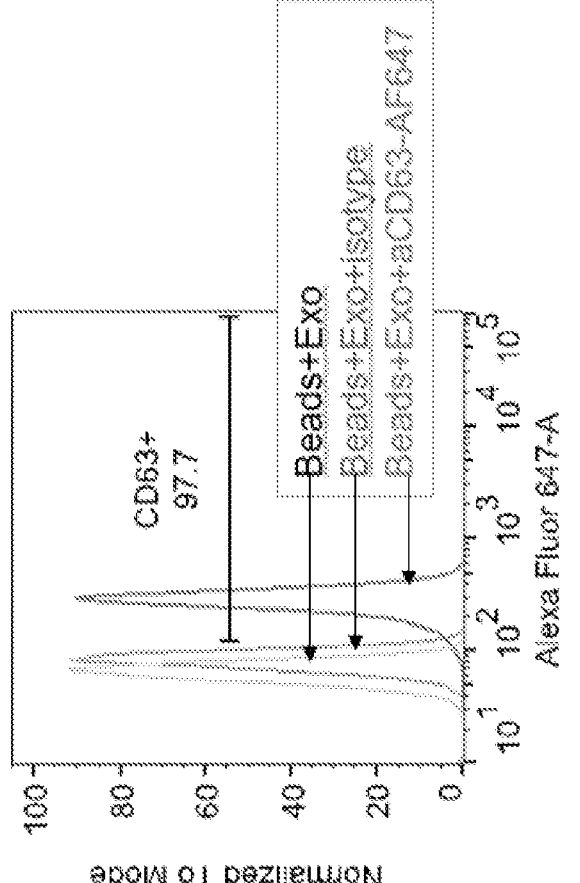
FIG. 6

A
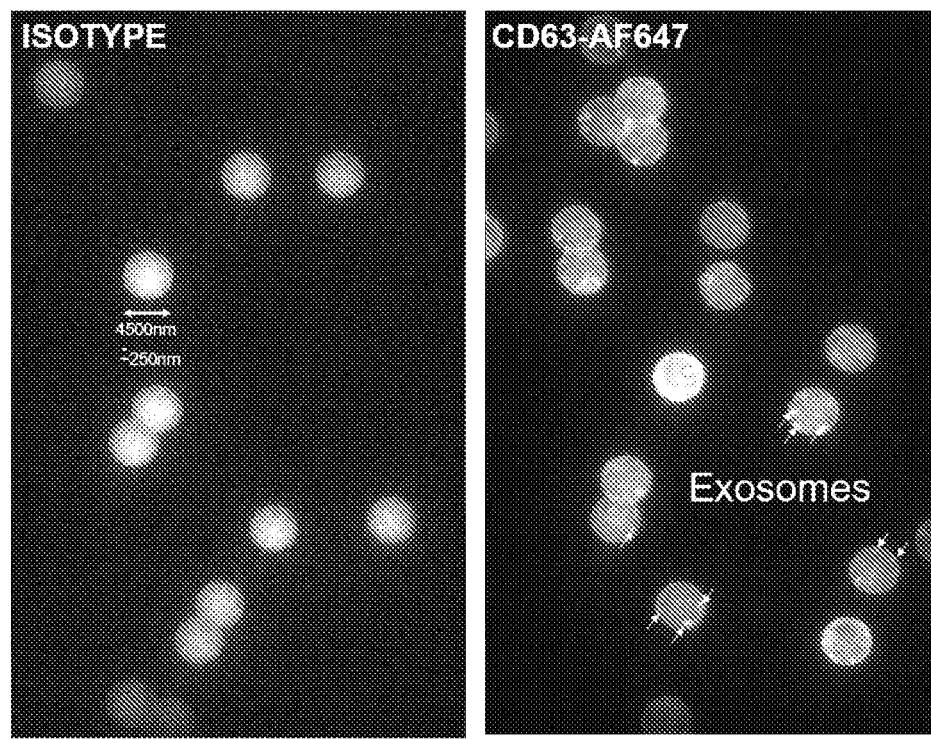
B
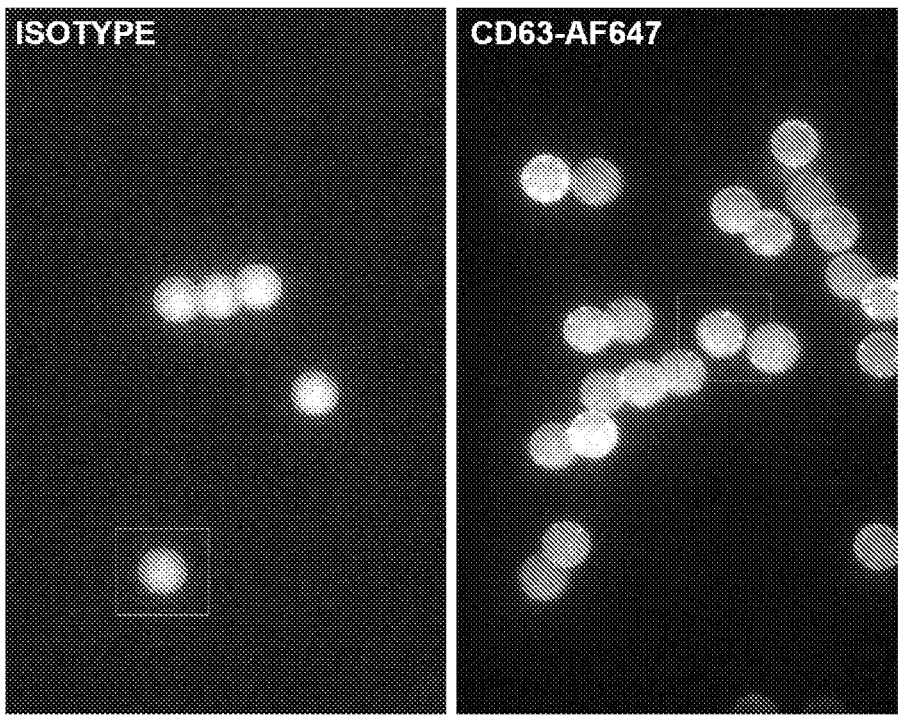
FIG. 8A-B

DIAGNOSTIC AND PROGNOSTIC UTILITY OF EXOSOMES IN IMMUNOTHERAPY

This application is a national phase application under 35 U.S.C. § 371 of International Application No. PCT/US2021/016887, filed Feb. 5, 2021, which claims the benefit of priority to U.S. Provisional Patent Application No. 62/970,611 filed Feb. 5, 2020, both of which are hereby incorporated by reference in their entirety.

BACKGROUND OF THE INVENTOR

Field of the Invention

This invention relates to the field of biotechnology and therapeutic treatment methods.

Background

Tremendous advances were made in cancer therapy in the past decade through the use of targeted therapy and immune therapy. By blocking immune inhibitory ligand-receptor interactions involving CTLA-4 and PD-1, checkpoint blockade immunotherapy relieves T lymphocytes of major inhibitory signals, thus potentiating underlying T cell-mediated anti-tumor immune activity. However, ubiquitous relief of inhibitory signals systemically can also activate T lymphocytes reactive against self-antigens, leading to loss of self-tolerance and immune-related adverse events. Patients who develop high-grade toxicities commonly require either temporary or permanent discontinuation of treatment, and may require prolonged periods of heavy immunosuppression in order to manage their toxicities. The high frequency of developing severe to life threatening toxicity to anti-CTLA-4 and/or anti-PD-1 therapy and the unpredictability with respect to whether a patient will respond has become a limiting factor for clinicians to prescribe this form of therapy.

While some factors associated with patient response to immune checkpoint inhibitor therapy have been discovered, there is a need in the art for predictors of toxicity due to immune checkpoint blockade therapy and predictors of responders to immune checkpoint blockade therapy. Stratifying patients into those that are likely and unlikely to respond to checkpoint blockade therapy, based on one or more biomarkers, will provide for more effective and therapeutic treatment methods for patients, since patients can be provided with the most effective therapy before further spreading of the disease.

SUMMARY OF THE INVENTION

The current disclosure provides for novel therapeutic methods by identifying patient populations that may be treated effectively by immunotherapies. It was found that responders of immunotherapeutic treatments have a higher amount of B-cell exosomes in their blood than non-responders. Aspects of the disclosure relate to a method of treating cancer in a subject comprising administering to the subject immune checkpoint blockade (ICB) therapy after B-cell exosomes have been detected in a biological sample from the subject.

Further aspects relate to A method for predicting a response to ICB therapy in a subject having cancer, the method comprising: (a) determining the amount of B-cell exosomes in a sample from the subject; (b) comparing the amount of B-cell exosomes in a sample from the subject to a control; and (c) detecting a differential amount of B cell exosomes compared to a control. In some embodiments, the method further comprises predicting that the patient will respond to the ICB therapy after (i) an increase in the amount of B-cell exosomes in a biological sample from the subject compared to a control has been detected, wherein the control represents an amount of B-cell exosomes in a biological sample from a subject that has been determined to not respond to ICB therapy; or (ii) an increase or a non-significantly different amount of B-cell exosomes compared to a control has been detected, wherein the control comprises an amount of B-cell exosomes in a biological sample from a subject that has been determined to respond to ICB therapy; or predicting that the patient will not respond to the ICB therapy after (i) a decrease in the amount of B-cell exosomes in a biological sample from the subject compared to a control has been detected, wherein the control represents an amount of B-cell exosomes in a biological sample from a subject that has been determined to respond to ICB therapy; or (ii) a decrease or a non-significantly different amount of B-cell exosomes compared to a control has been detected, wherein the control comprises an amount of B-cell exosomes in a biological sample from a subject that has been determined to not respond to ICB therapy. In some embodiments, (c) comprises detecting (i) an increase in the amount of B-cell exosomes in a biological sample from the subject compared to a control, wherein the control represents an amount of B-cell exosomes in a biological sample from a subject that has been determined to not respond to ICB therapy; or (ii) an increase or a non-significantly different amount of B-cell exosomes compared to a control, wherein the control comprises an amount of B-cell exosomes in a biological sample from a subject that has been determined to respond to ICB therapy. In some embodiments, (c) comprises detecting (i) a decrease in the amount of B-cell exosomes in a biological sample from the subject compared to a control, wherein the control represents an amount of B-cell exosomes in a biological sample from a subject that has been determined to respond to ICB therapy; or (ii) a decrease or a non-significantly different amount of B-cell exosomes compared to a control, wherein the control comprises an amount of B-cell exosomes in a biological sample from a subject that has been determined to not respond to ICB therapy.

Further aspects relate to a method for predicting a response to ICB therapy in a subject having cancer, the method comprising: (a) determining the amount of B-cell exosomes in a sample from the subject; (b) comparing the amount of B-cell exosomes in a sample from the subject to a control; and (c) predicting that the patient will respond to the ICB therapy after (i) an increase in the amount of B-cell exosomes in a biological sample from the subject compared to a control has been detected, wherein the control represents an amount of B-cell exosomes in a biological sample from a subject that has been determined to not respond to ICB therapy; or (ii) an increase or a non-significantly different amount of B-cell exosomes compared to a control has been detected, wherein the control comprises an amount of B-cell exosomes in a biological sample from a subject that has been determined to respond to ICB therapy; or (d) predicting that the patient will not respond to the ICB therapy after (i) a decrease in the amount of B-cell exosomes in a biological sample from the subject compared to a control has been detected, wherein the control represents an amount of B-cell exosomes in a biological sample from a subject that has been determined to respond to ICB therapy; or (ii) a decrease or a non-significantly different amount of B-cell exosomes compared to a control has been detected, wherein the control comprises an amount of B-cell exosomes in a biological sample from a subject that has been determined to not respond to ICB therapy. Other aspects of the disclosure relate to s method comprising detecting B-cell exosomes in a subject with cancer.

Further aspects relate to a method for monitoring a subject being treated with ICB therapy, the method comprising evaluating B-cell exosomes in the subject. The exosomes may be evaluated in the subject, before ICB therapy, after at least one dose of ICB therapy, or after multiple doses of ICB therapy, such as after 2, 3, 4, 5, or 6 doses.

In some embodiments, the subject has been determined to have an increase in the amount of B-cell exosomes in comparison to a control, wherein the control represents an amount of B-cell exosomes in a biological sample from a subject that has been determined to not respond effectively to ICB therapy. In some embodiments, the amounts are standardized, such as through measurement of a standard control. In some embodiments, the increase is at least 1.5, 2, 2.5, 3, 3.5, 4, 4.5, 5, 5.5, 6, 6.5, 7, 7.5, 8, 8.5, 9, 9.5, or 10 times more than the control. In some embodiments, the subject has been determined to have an amount of B-cell exosomes that is not significantly different or is more than a control amount, wherein the control represents an amount of B-cell exosomes in a biological sample from a subject that has been determined to respond effectively to ICB therapy. In some embodiments, the determined amount is not significantly different than the control. In some embodiments, the determined amount is less than 1, 2, 3, or 4 standard deviations (or any derivable range therein) from the control.

In some embodiments, the cancer comprises a skin cancer. In some embodiments, the cancer comprises basal-cell skin cancer, squamous-cell skin cancer, melanoma, dermatofibrosarcoma protuberans, Merkel cell carcinoma, Kaposi's sarcoma, keratoacanthoma, spindle cell tumors, sebaceous carcinomas, microcystic adnexal carcinoma, Paget's disease of the breast, atypical fibroxanthoma, leiomyosarcoma, or angiosarcoma. In some embodiments, the cancer comprises melanoma, metastatic melanoma, Lentigo Maligna, Lentigo Maligna Melanoma, Superficial Spreading Melanoma, Nodular Melanoma, Acral Lentiginous Melanoma, Cutaneous Melanoma, or Desmoplastic Melanoma.

In some embodiments, the method further comprises administering at least one additional anticancer treatment/therapy. In some embodiments, the at least one additional anticancer treatment is surgical therapy, chemotherapy, radiation therapy, hormonal therapy, immunotherapy, small molecule therapy, receptor kinase inhibitor therapy, antiangiogenic therapy, cytokine therapy, cryotherapy or a biological therapy. In some embodiments, the additional therapy is one described herein.

In some embodiments, the ICB therapy comprises a mono ICB therapy. In some embodiments, the ICB therapy comprises combination ICB therapy. The term "mono ICB therapy" refers to administration of a single immune checkpoint blockade inhibitor agent, such as an anti-PD1 antibody or an anti-CTLA4 antibody alone. The term "combination ICB therapy" refers to administration of at least two immune checkpoint blockade inhibitor agents, such as an anti-PD1 antibody and an anti-CTLA4 antibody alone. The two agents in combination ICB therapy are typically directed to one of each of (a) and (b), wherein (a) comprises PDL1, PD1, and PDL2 and (b) comprises CTLA-4, B7-1 and B7-2. In some embodiments, the ICB therapy comprises an inhibitor of PD-1, PDL1, PDL2, CTLA-4, B7-1, and/or B7-2. In some embodiments, the ICB therapy comprises an anti-PD-1 monoclonal antibody and/or an anti-CTLA-4 monoclonal antibody. In some embodiments, the ICB therapy comprises one or more of nivolumab, pembrolizumab, pidilizumab, ipilimumab or tremelimumab. In some embodiments, the subject has been determined to be a candidate for ICB therapy. In some embodiments, the subject is currently being treated with ICB therapy. In some embodiments, the subject has received at least one ICB therapy. In some embodiments, the subject has received at least one, 2, 3, 4, 5, or 6 doses (or any derivable range therein) of ICB therapy within 1, 2, 3, 4, 5, 6, 7, 8, 9, 10, 12, 16, 20, 24, 28, 32, 36, 40, 44, 48, or 52 weeks (or any derivable range therein). In some embodiments, the subject has not been treated with ICB therapy.

In some embodiments, the method further comprises comparing the amount of detected B-cell exosomes to a control. In some embodiments, he control comprises an amount of B-cell exosomes in a biological sample from a subject that does not respond to ICB therapy. In some embodiments, the control comprises an amount of B-cell exosomes in a biological sample from a subject that responds to ICB therapy.

In some embodiments, the B-cell exosomes are further defined as positive for one or more of CD63, CD9, CD20, CD27, and/or GPC1. In some embodiments, the B-cell exosomes were detected or are determined by an immunocapture assay. In some embodiments, CD63+ exosomes were detected in a biological sample and/or were detected in an immunocapture assay.

In some embodiments, the biological sample comprises a blood sample, a serum sample, a plasma sample, or a fraction of a blood, serum, or plasma sample. In some embodiments, the biological sample comprises a serum sample. In some embodiments, the biological sample comprises a plasma sample. The sample may be frozen or fresh and can be thawed prior to use.

In some embodiments, the subject is determined to have a higher amount of B-cell exosomes than the control. In some embodiments, the increase is at least 1.5, 2, 2.5, 3, 3.5, 4, 4.5, 5, 5.5, 6, 6.5, 7, 7.5, 8, 8.5, 9, 9.5, or 10 times more than the control. In some embodiments, the subject is determined to have the same, less, or substantially the same amount of B-cell exosomes than the control. In some embodiments, the amount of B cells in the biological sample from the patient is less than 1, 2, 3, or 4 standard deviations (or any derivable range therein) from the control. In some embodiments, the subject is determined to have a lower amount of B-cell exosomes than the control.

The evaluated, measured, or determined exosome level may be a normalized level. In some embodiments, the level of exosomes is determined to be greater than a control. In some embodiments, the level of exosomes is determined to be less than a control.

Method of the disclosure may include detecting, evaluating, measuring the amount of, and/or quantitating B-cell exosomes in a biological sample. The biological sample may be one that has been subjected to a method of B-cell exosome isolation described herein. The biological sample may comprise a sample that has been filtered through a filter of a certain pore size. In some embodiments, the supernatant of the sample after centrifugation is filtered and used for exosome analysis and/or further exosome isolation steps. In some embodiments, the biological sample comprises a sample that has undergone ultracentrifugation. In some embodiments, the biological sample comprises a sample that has undergone FACS analysis or an immunoanalysis to detect markers. Methods of the disclosure may also include filtering the biological sample through a filter of a certain pore size. Method embodiments also include ultracentrifugation of the sample or filtered sample. Methods also include analysis of the sample, such as immunological analysis. The analysis may comprise FACS analysis, analysis with an immunocapture assay, nanoimager analysis, electron microscopy analysis, and combinations thereof.

The filter pore size in embodiments may be at least, at most, or exactly 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, or 0.4, μm, or any derivable range therein. In some embodiments, the filter has a pore size of 0.22 μm. In some embodiments, the filtrate is subjected to ultracentrifugation for at least, at most, or about 6, 7, 8, 9, 10, 11, 12, 13, 14, 15, 16, 17, 18, 19, 20, 21, 22, 23, or 24 hours (or any derivable range therein) at 100,000 g. In some embodiments, the sample is subjected to ultracentrifugation at least, at most, or about 40000, 50000, 60000, 70000, 80000, 90000, 100000, 110000, 120000, 130000, 140000, 150000, 160000, 170000, 180000, 190000, or 200000 g (or any derivable range therein). The pellet from the ultracentrifugation may contain the exosomes, which then may be further analyzed and characterized or frozen for further use. In some embodiments, the exosomes are frozen. In some embodiments, the exosomes are fresh.

The exosomes may be further analyzed with labeled antibodies or controls such as anti-human CD20, anti-human CD27, anti-human CD9, and anti-human CD63. In some embodiments, the exosomes may be subject to GPC1 staining.

Throughout this application, the term "about" is used according to its plain and ordinary meaning in the area of cell and molecular biology to indicate that a value includes the standard deviation of error for the device or method being employed to determine the value.

The use of the word "a" or "an" when used in conjunction with the term "comprising" may mean "one," but it is also consistent with the meaning of "one or more," "at least one," and "one or more than one."

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment.

The words "comprising" (and any form of comprising, such as "comprise" and "comprises"), "having" (and any form of having, such as "have" and "has"), "including" (and any form of including, such as "includes" and "include"), "characterized by" (and any form of including, such as "characterized as"), or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. The phrase "consisting of" excludes any element, step, or ingredient not specified. The phrase "consisting essentially of" limits the scope of described subject matter to the specified materials or steps and those that do not materially affect its basic and novel characteristics. It is contemplated that embodiments described in the context of the term "comprising" may also be implemented in the context of the term "consisting of" or "consisting essentially of."

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. Aspects of an embodiment set forth in the Examples are also embodiments that may be implemented in the context of embodiments discussed elsewhere in a different Example or elsewhere in the application, such as in the Summary of Invention, Detailed Description of the Embodiments, Claims, and description of Figure Legends.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-H. Increase in B-cell related exosomes in serum of responders to immune checkpoint blockade (ICB). A. Schematic for exosomal analyses of serum samples from melanoma patients on neoadjuvant ICB trial. B. Representative transmission electron micrographs showing DYnabead with exosome present following immunocapture. C. Nanoimager-captured images of the beads coated with CD63+ exosomes. Isotype control shown. Exosomal concentration (D) and mean exosomal size (e) for serum samples for responders (Rs) and non-responders (NRs) at timepoint indicated. F. Percentage of exosome-coated beads staining positive for CD63 after immunocapture. G. Percentage of exosome-coated beads positive for CD9, CD20, CD27, and GPC1 as indicated. H. Ratio of MFI of beads stained with CD9, CD20, CD27, and GPC1 and isotype control (or secondary antibody only for GPC1). For all plots, bars indicate median values and individual data points representing 8 R and 5 NR (unless indicated in Example 1) in addition to interquartile ranges are shown. Comparisons made using two-sided Mann-Whitney U tests are shown. For (D) and (€) Kruskall-Wallis was used and showed no significant differences between the samples.

FIG. 3. Exosomes immunocapture (ImC.) with anti-CD63; FC with AF647-anti-CD63. The beads (FIG. 2) are analyzed by flow cytometry and the results show positive signal with conjugated anti-CD63 antibodies, supporting successful immunocapture of CD63+ exosomes on the Dynabeads. The isotype control show little/no positivity, supporting specific capture of positive beads using conjugated anti-CD63 antibodies.

FIG. 6. Exosomes immunocapture (ImC.) with anti-CD63; FC with AF647-anti-CD63: Normalized MFI (MFI$^{CD63}$/MFI$^{Isotype}$). Graphed data for the MFI (mean fluorescence intensity) of CD63+ beads for each patient sample analyzed. BL, baseline; OT, on treatment; NR, non-responder; R: responder. The MFI CD63+ beads in similar in all samples studied. ns: not significant.

FIG. 8A-C. Nanoimager-captured images of isotype control and CD63-AF647. A. Representative images from nanoimager showing Dynabeads with immunocapture of CD63+ exosomes. Isotype: control. B. Representative images from nanoimager showing Dynabeads with immunocapture of CD63+ exosomes. Isotype: control. C. Representative images from nanoimager showing Dynabeads with immunocapture of CD63+ exosomes. Isotype: control. Arrows point to positive signal.

FIG. 9. Exosomes immunocapture (ImC.) with anti-CD63; FC with PE/Cy7-anti-CD20: Normalized MFI (MFI$^{CD20}$/MFI$^{Isotype}$) Graphed data for the Log 2 MFI (mean fluorescence intensity) of CD20+ of beads with immunocapture of CD63+ exosomes for each patient sample analyzed. BL, baseline; OT, on treatment; NR, non-responder; R: responder. The MFI CD20+ beads in greater in responders on treatment.

DETAILED DESCRIPTION OF THE INVENTION

Figure 2:
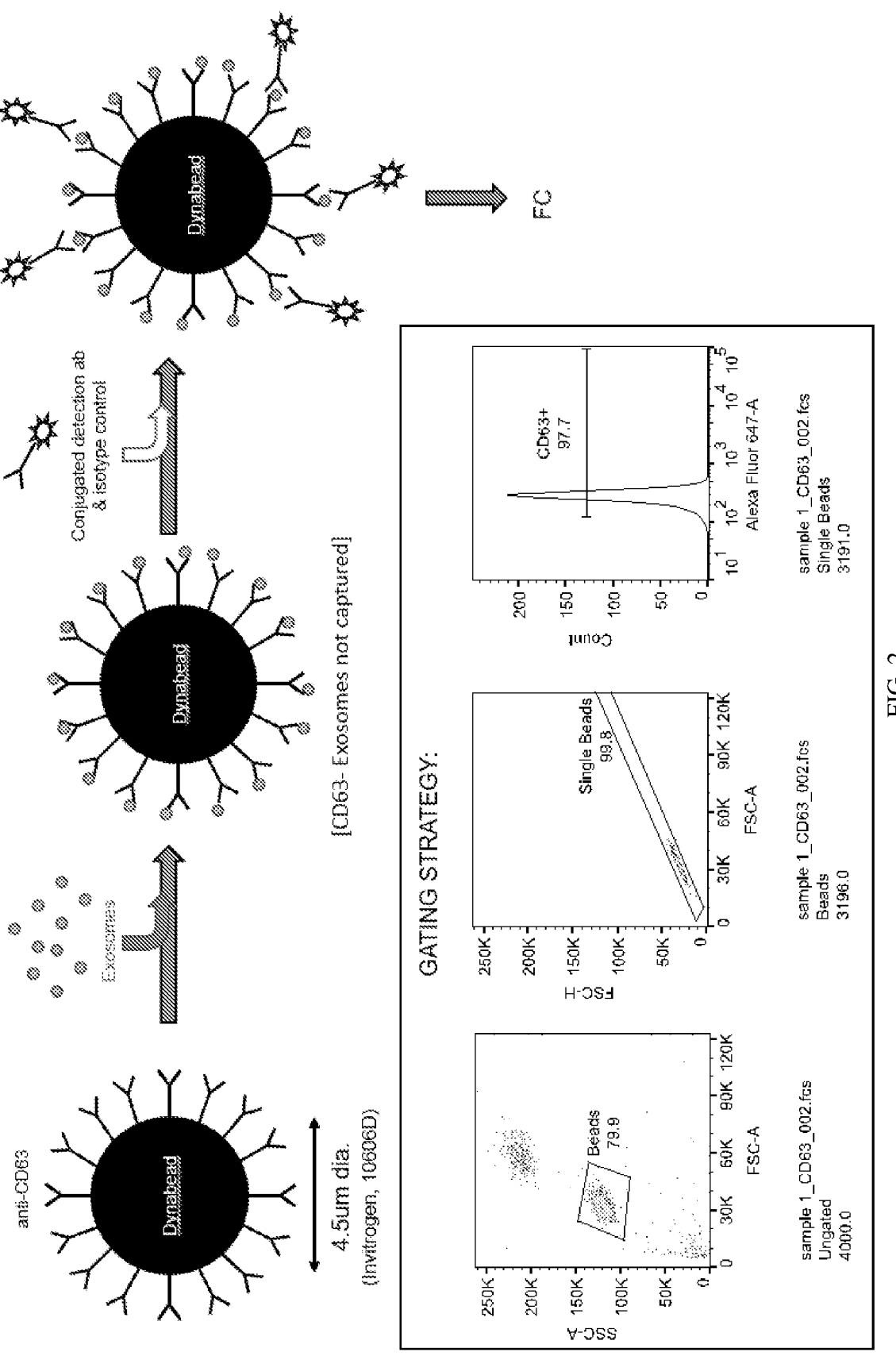
FIG. 2. Exosomes immunocapture with anti-CD63. Exosomes were purified by ultracentrifugation and filtration from the de-identified plasma of cancer patients. The exosomes were immunocaptured using Dynabeads coated with anti-CD64 antibodies. CD63+ exosomes, bound to the Dynabeads, were then immunolabeled using conjugated anti-CD63 antibodies or an isotype control. The beads are analyzed by flow cytometry and the results show positive signal with conjugated anti-CD63 antibodies, supporting successful immunocapture of CD63+ exosomes on the Dynabeads. CD63 is an exosomes marker.
Figure 4:
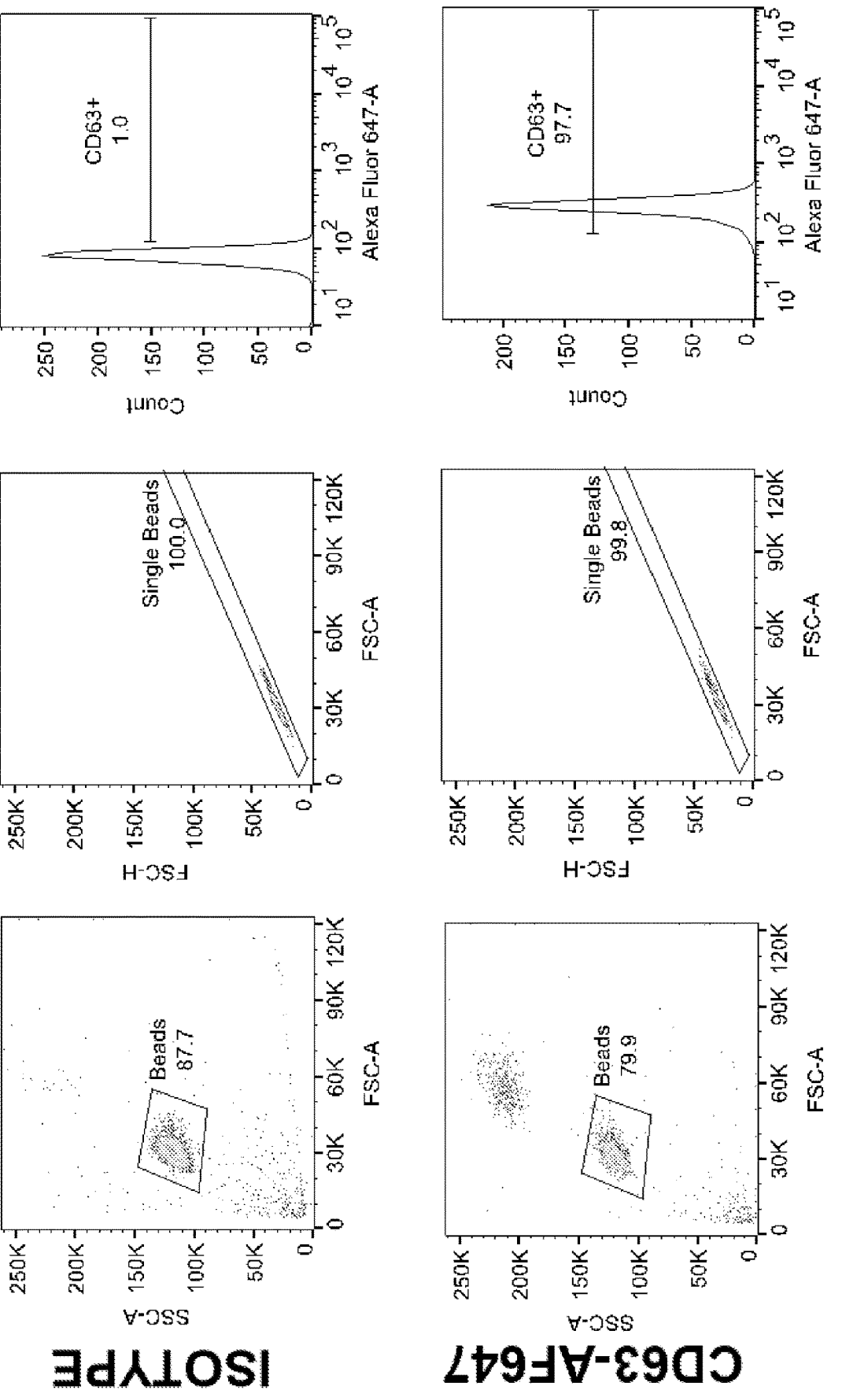
FIG. 4. Exosomes immunocapture (ImC.) with anti-CD63; FC with AF647-anti-CD63 (Gating strategy). Representative flow cytometry gating strategy for the immunocapture of CD63+ exosomes on the Dynabeads. Isotype: control.
Figure 5:
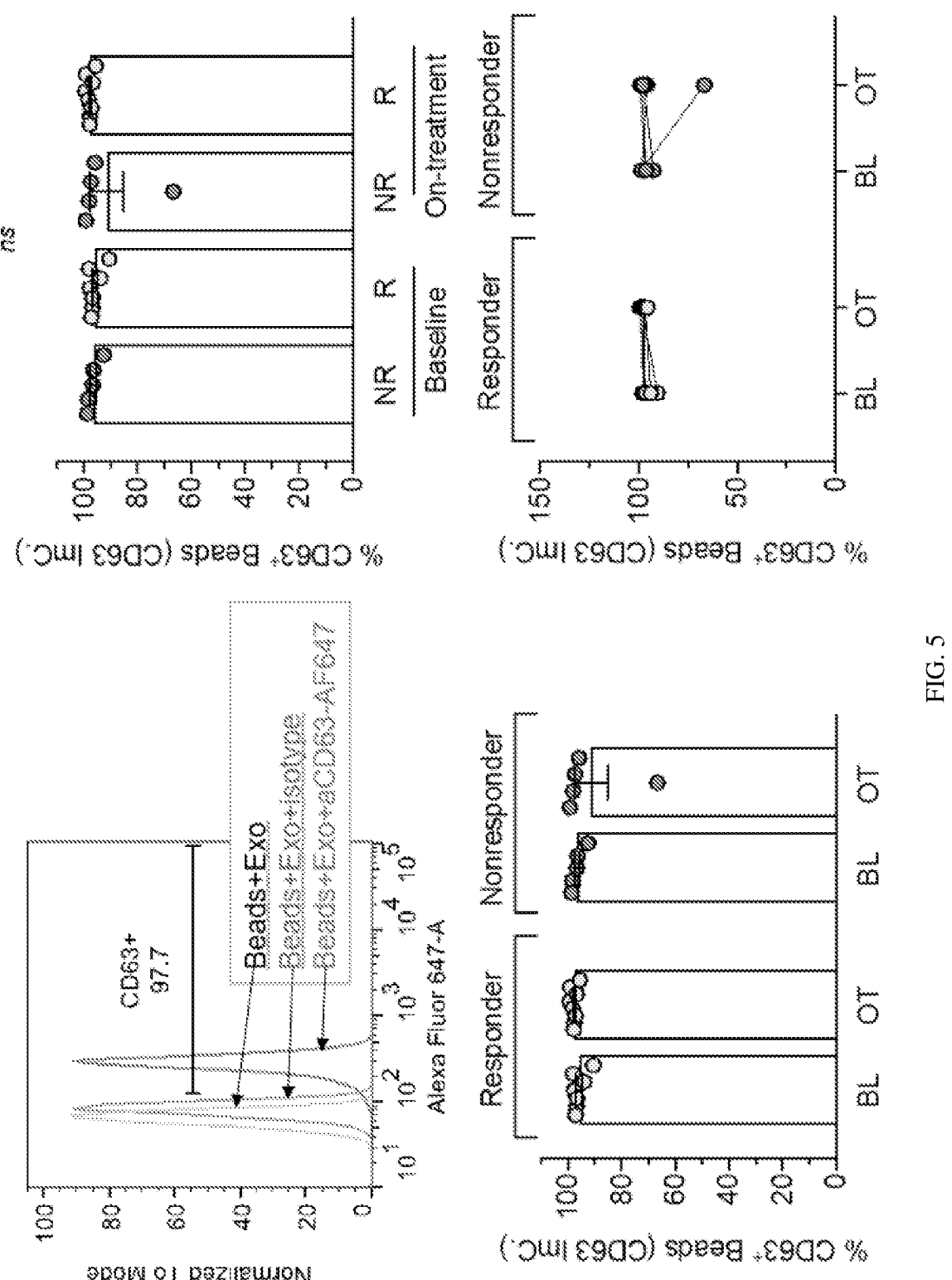
FIG. 5. Exosomes immunocapture (ImC.) with anti-CD63; FC with AF647-anti-CD63: % positive beads (isotype<1%). Graphed data for the % CD63+ beads for each patient sample analyzed. BL, baseline; OT, on treatment; NR, non-responder; R: responder. The percent CD63+ beads in similar in all samples studied.

Extracellular vesicles (EVs), including exosomes and microvesicles, are nano-sized particles that participate in several physiological processes. The role of exosomes in immune response and immune-mediated diseases is still being explored. Whether exosomes carry proteins associated with immune cells, such as B cells and T cells was probed in the context of immune checkpoint blockade therapy. It was discovered that the blood of cancer patients contain exosomes with markers of B cell (B cell exosomes) that are useful for tracking tumor burden and can predict immunotherapy responders. Therefore, the current methods can be used to identify a population of patients that may respond to an immunotherapy, such as checkpoint inhibitor blockade therapy.

I. ISOLATION AND CHARACTERIZATION OF EXOSOMES

Methods for isolating and characterizing exosomes are known in the art. Described below is a method that can be used to isolate and characterize exosomes.

A. Isolation of Exosomes from Human Plasma.

Plasma, blood, a fractionated sample, or any other biological sample may be obtained from a patient. The sample may be frozen or fresh and can be thawed prior to use. The sample can be centrifuged and a fraction of the sample may be used for exosome isolation. In some embodiments, the supernatant of the sample after centrifugation is filtered and used for exosome analysis and/or further exosome isolation steps. For example, the sample may be filtered through a filter with a pore size that is at least, at most, or exactly 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, or 0.4, μm, or any derivable range therein. In some embodiments, the filter has a pore size of 0.22 μm. In some embodiments, the filtrate is subjected to ultracentrifugation for at least, at most, or about 6, 7, 8, 9, 10, 11, 12, 13, 14, 15, 16, 17, 18, 19, 20, 21, 22, 23, or 24 hours (or any derivable range therein) at 100,000 g. In some embodiments, the sample is subjected to ultracentrifugation at least, at most, or about 40000, 50000, 60000, 70000, 80000, 90000, 100000, 110000, 120000, 130000, 140000, 150000, 160000, 170000, 180000, 190000, or 200000 g (or any derivable range therein). The pellet from the ultracentrifugation may contain the exosomes, which then may be further analyzed and characterized or frozen for further use. In some embodiments, the exosomes are frozen. In some embodiments, the exosomes are fresh.

B. Flow Cytometry Analyses of Exosomes.

In some embodiments, exosomes are analyzed and characterized by flow cytometry. Exosomes can be thawed on ice. Concentration can be determined using the NanoSight NS300 nanoparticle tracking analyzer according to the manufacturer's directions. The exosomes may be analyzed for CD63 expression by mixing the sample with anti-human CD63-coated Dynabeads® (Invitrogen, 10606D), for example, and the unbound portion may be removed after a sufficient period of time. The beads may be washed to further remove non-specific binding.

The exosomes may be further analyzed with labeled antibodies or controls such as anti-human CD20, anti-human CD27, anti-human CD9, and anti-human CD63. In some embodiments, the exosomes may be subject to GPC1 staining.

C. Nanoimager Analyses.

Beads with exosomes stained for flow cytometry analysis for a marker such as CD63 can be evaluated by using the on the Nanoimager S Mark I from ONI (Oxford Nanoimaging) with the lasers 405 nm/150 mW, 488 nm/200 mW, 561 nm/300 mW, 640 nm/1 W and dual emission channels split at 560 nm. Data can be processed on NimOS (Version [1.25]) from ONI.

D. Electron Microscopy Analyses.

In some embodiments, the exosome preparation may be analyzed by electron microscopy analysis. The exosome preparation (such as CD63 dynabead-bound exosome preparation) may be magnetized and resuspended in glutaraldehyde/PBS or BSA/PBS, and 680 with warm agarose in distilled water. The agarose-bead mixture can then be cooled and cut into pieces and placed glutaraldehyde/PBS for fixation. Fixed samples can be washed with a buffer and treated with cacodylate buffered tannic acid, postfixed with buffered osmium, and stained en bloc with 1 uranyl acetate. The samples can then be dehydrated in increasing concentrations of ethanol, infiltrated, and embedded in LX-112 medium. The samples may be polymerized in an oven for 1, 2, 3, 4, 5, or 6 days, for example. Sections may then be cut, stained and examined in a JEM 1010 transmission electron microscope (JEOL, USA, Inc., 689 Peabody, MA) at an accelerating voltage of 80 kV. Digital images may then be obtained using AMT 690 Imaging System (Advanced Microscopy Techniques Corp, Danvers, MA) and analyzed.

II. IMMUNOTHERAPY

In some embodiments, the methods comprise administration of a cancer immunotherapy. Cancer immunotherapy (sometimes called immuno-oncology, abbreviated IO) is the use of the immune system to treat cancer. Immunotherapies can be categorized as active, passive or hybrid (active and passive). These approaches exploit the fact that cancer cells often have molecules on their surface that can be detected by the immune system, known as tumour-associated antigens (TAAs); they are often proteins or other macromolecules (e.g. carbohydrates). Active immunotherapy directs the immune system to attack tumor cells by targeting TAAs. Passive immunotherapies enhance existing anti-tumor responses and include the use of monoclonal antibodies, lymphocytes and cytokines. Immunotherapies are known in the art, and some are described below.

A. Immune Checkpoint Blockade Therapy

Embodiments of the disclosure may include administration of immune checkpoint blockade therapy, which are further described below.

1. PD-1, PDL1, and PDL2 Inhibitors

PD-1 can act in the tumor microenvironment where T cells encounter an infection or tumor. Activated T cells upregulate PD-1 and continue to express it in the peripheral tissues. Cytokines such as IFN-gamma induce the expression of PDL1 on epithelial cells and tumor cells. PDL2 is expressed on macrophages and dendritic cells. The main role of PD-1 is to limit the activity of effector T cells in the periphery and prevent excessive damage to the tissues during an immune response. Inhibitors of the disclosure may block one or more functions of PD-1 and/or PDL1 activity.

Alternative names for "PD-1" include CD279 and SLEB2. Alternative names for "PDL1" include B7-H1, B7-4, CD274, and B7-H. Alternative names for "PDL2" include B7-DC, Btdc, and CD273. In some embodiments, PD-1, PDL1, and PDL2 are human PD-1, PDL1 and PDL2.

In some embodiments, the PD-1 inhibitor is a molecule that inhibits the binding of PD-1 to its ligand binding partners. In a specific aspect, the PD-1 ligand binding partners are PDL1 and/or PDL2. In another embodiment, a PDL1 inhibitor is a molecule that inhibits the binding of PDL1 to its binding partners. In a specific aspect, PDL1 binding partners are PD-1 and/or B7-1. In another embodiment, the PDL2 inhibitor is a molecule that inhibits the binding of PDL2 to its binding partners. In a specific aspect, a PDL2 binding partner is PD-1. The inhibitor may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 inhibitors for use in the methods and compositions provided herein are known in the art such as described in U.S. Patent Application Nos. US2014/0294898, US2014/022021, and US2011/0008369, all incorporated herein by reference.

In some embodiments, the PD-1 inhibitor is an anti-PD-1 antibody (e.g., a human antibody, a humanized antibody, or a chimeric antibody). In some embodiments, the anti-PD-1 antibody is selected from the group consisting of nivolumab, pembrolizumab, and pidilizumab. In some embodiments, the PD-1 inhibitor is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PDL1 inhibitor comprises AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. Pidilizumab, also known as CT-011, hBAT, or hBAT-1, is an anti-PD-1 antibody described in WO2009/101611. AMP-224, also known as B7-DCIg, is a PDL2-Fc fusion soluble receptor described in WO2010/027827 and WO2011/066342. Additional PD-1 inhibitors include MEDI0680, also known as AMP-514, and REGN2810.

In some embodiments, the ICB therapy comprises a PDL1 inhibitor such as Durvalumab, also known as MEDI4736, atezolizumab, also known as MPDL3280A, avelumab, also known as MSB00010118C, MDX-1105, BMS-936559, or combinations thereof. In certain aspects, the ICB therapy comprises a PDL2 inhibitor such as rHIgM12B7.

In some embodiments, the inhibitor comprises the heavy and light chain CDRs or VRs of nivolumab, pembrolizumab, or pidilizumab. Accordingly, in one embodiment, the inhibitor comprises the CDR1, CDR2, and CDR3 domains of the VH region of nivolumab, pembrolizumab, or pidilizumab, and the CDR1, CDR2 and CDR3 domains of the VL region of nivolumab, pembrolizumab, or pidilizumab. In another embodiment, the antibody competes for binding with and/or binds to the same epitope on PD-1, PDL1, or PDL2 as the above-mentioned antibodies. In another embodiment, the antibody has at least about 70, 75, 80, 85, 90, 95, 97, or 99% (or any derivable range therein) variable region amino acid sequence identity with the above-mentioned antibodies.

2. CTLA-4, B7-1, and B7-2

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to B7-1 (CD80) or B7-2 (CD86) on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to B7-1 and B7-2 on antigen-presenting cells. CTLA-4 transmits an inhibitory signal to T cells, whereas CD28 transmits a stimulatory signal. Intracellular CTLA-4 is also found in regulatory T cells and may be important to their function. T cell activation through the T cell receptor and CD28 leads to increased expression of CTLA-4, an inhibitory receptor for B7 molecules. Inhibitors of the disclosure may block one or more functions of CTLA-4, B7-1, and/or B7-2 activity. In some embodiments, the inhibitor blocks the CTLA-4 and B7-1 interaction. In some embodiments, the inhibitor blocks the CTLA-4 and B7-2 interaction.

In some embodiments, the ICB therapy comprises an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al., 1998; can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001/014424, WO2000/037504, and U.S. Pat. No. 8,017,114; all incorporated herein by reference.

A further anti-CTLA-4 antibody useful as an ICB therapy in the methods and compositions of the disclosure is ipilimumab (also known as 10D1, MDX-010, MDX-101, and Yervoy®) or antigen binding fragments and variants thereof (see, e.g., WOO 1/14424).

In some embodiments, the inhibitor comprises the heavy and light chain CDRs or VRs of tremelimumab or ipilimumab. Accordingly, in one embodiment, the inhibitor comprises the CDR1, CDR2, and CDR3 domains of the VH region of tremelimumab or ipilimumab, and the CDR1, CDR2 and CDR3 domains of the VL region of tremelimumab or ipilimumab. In another embodiment, the antibody competes for binding with and/or binds to the same epitope on PD-1, B7-1, or B7-2 as the above-mentioned antibodies. In another embodiment, the antibody has at least about 70, 75, 80, 85, 90, 95, 97, or 99% (or any derivable range therein) variable region amino acid sequence identity with the above-mentioned antibodies.

B. Activation of Co-Stimulatory Molecules

In some embodiments, the immunotherapy comprises an activator of a co-stimulatory molecule. In some embodiments, the inhibitor comprises an inhibitor of B7-1 (CD80), B7-2 (CD86), CD28, ICOS, OX40 (TNFRSF4), 4-1BB (CD137; TNFRSF9), CD40L (CD40LG), GITR (TN-FRSF18), and combinations thereof. Inhibitors include inhibitory antibodies, polypeptides, compounds, and nucleic acids.

C. Dendritic Cell Therapy

Dendritic cell therapy provokes anti-tumor responses by causing dendritic cells to present tumor antigens to lymphocytes, which activates them, priming them to kill other cells that present the antigen. Dendritic cells are antigen presenting cells (APCs) in the mammalian immune system. In cancer treatment they aid cancer antigen targeting. One example of cellular cancer therapy based on dendritic cells is sipuleucel-T.

One method of inducing dendritic cells to present tumor antigens is by vaccination with autologous tumor lysates or short peptides (small parts of protein that correspond to the protein antigens on cancer cells). These peptides are often given in combination with adjuvants (highly immunogenic substances) to increase the immune and anti-tumor responses. Other adjuvants include proteins or other chemicals that attract and/or activate dendritic cells, such as granulocyte macrophage colony-stimulating factor (GM-CSF).

Dendritic cells can also be activated in vivo by making tumor cells express GM-CSF. This can be achieved by either genetically engineering tumor cells to produce GM-CSF or by infecting tumor cells with an oncolytic virus that expresses GM-CSF.

Another strategy is to remove dendritic cells from the blood of a patient and activate them outside the body. The dendritic cells are activated in the presence of tumor antigens, which may be a single tumor-specific peptide/protein or a tumor cell lysate (a solution of broken down tumor cells). These cells (with optional adjuvants) are infused and provoke an immune response.

Dendritic cell therapies include the use of antibodies that bind to receptors on the surface of dendritic cells. Antigens can be added to the antibody and can induce the dendritic cells to mature and provide immunity to the tumor. Dendritic cell receptors such as TLR3, TLR7, TLR8 or CD40 have been used as antibody targets.

D. CAR-T Cell Therapy

Chimeric antigen receptors (CARs, also known as chimeric immunoreceptors, chimeric T cell receptors or artificial T cell receptors) are engineered receptors that combine a new specificity with an immune cell to target cancer cells. Typically, these receptors graft the specificity of a monoclonal antibody onto a T cell. The receptors are called chimeric because they are fused of parts from different sources. CAR-T cell therapy refers to a treatment that uses such transformed cells for cancer therapy.

The basic principle of CAR-T cell design involves recombinant receptors that combine antigen-binding and T-cell activating functions. The general premise of CAR-T cells is to artificially generate T-cells targeted to markers found on cancer cells. Scientists can remove T-cells from a person, genetically alter them, and put them back into the patient for them to attack the cancer cells. Once the T cell has been engineered to become a CAR-T cell, it acts as a "living drug". CAR-T cells create a link between an extracellular ligand recognition domain to an intracellular signalling molecule which in turn activates T cells. The extracellular ligand recognition domain is usually a single-chain variable fragment (scFv). An important aspect of the safety of CAR-T cell therapy is how to ensure that only cancerous tumor cells are targeted, and not normal cells. The specificity of CAR-T cells is determined by the choice of molecule that is targeted.

Exemplary CAR-T therapies include Tisagenlecleucel (Kymriah) and Axicabtagene ciloleucel (Yescarta). In some embodiments, the CAR-T therapy targets CD19.

E. Cytokine Therapy

Cytokines are proteins produced by many types of cells present within a tumor. They can modulate immune responses. The tumor often employs them to allow it to grow and reduce the immune response. These immune-modulating effects allow them to be used as drugs to provoke an immune response. Two commonly used cytokines are interferons and interleukins.

Interferons are produced by the immune system. They are usually involved in anti-viral response, but also have use for cancer. They fall in three groups: type I (IFNα and IFNβ), type II (IFNγ) and type III (IFNλ).

Interleukins have an array of immune system effects. IL-2 is an exemplary interleukin cytokine therapy.

F. Adoptive T-Cell Therapy

Adoptive T cell therapy is a form of passive immunization by the transfusion of T-cells (adoptive cell transfer). They are found in blood and tissue and usually activate when they find foreign pathogens. Specifically they activate when the T-cell's surface receptors encounter cells that display parts of foreign proteins on their surface antigens. These can be either infected cells, or antigen presenting cells (APCs). They are found in normal tissue and in tumor tissue, where they are known as tumor infiltrating lymphocytes (TILs). They are activated by the presence of APCs such as dendritic cells that present tumor antigens. Although these cells can attack the tumor, the environment within the tumor is highly immunosuppressive, preventing immune-mediated tumour death.[60]

Multiple ways of producing and obtaining tumour targeted T-cells have been developed. T-cells specific to a tumor antigen can be removed from a tumor sample (TILs) or filtered from blood. Subsequent activation and culturing is performed ex vivo, with the results reinfused. Activation can take place through gene therapy, or by exposing the T cells to tumor antigens.

It is contemplated that a cancer treatment may exclude any of the cancer treatments described herein. Furthermore, embodiments of the disclosure include patients that have been previously treated for a therapy described herein, are currently being treated for a therapy described herein, or have not been treated for a therapy described herein. In some embodiments, the patient is one that has been determined to be resistant to a therapy described herein. In some embodiments, the patient is one that has been determined to be sensitive to a therapy described herein.

III. ADDITIONAL THERAPIES

The current methods and compositions of the disclosure may include one or more additional therapies known in the art and/or described herein. In some embodiments, the additional therapy comprises an additional cancer treatment. Examples of such treatments are described herein, such as the immunotherapies described herein or the additional therapy types described in the following.

A. Oncolytic Virus

In some embodiments, the additional therapy comprises an oncolytic virus. An oncolytic virus is a virus that preferentially infects and kills cancer cells. As the infected cancer cells are destroyed by oncolysis, they release new infectious virus particles or virions to help destroy the remaining tumor. Oncolytic viruses are thought not only to cause direct destruction of the tumor cells, but also to stimulate host anti-tumor immune responses for long-term immunotherapy B. Polysaccharides In some embodiments, the additional therapy comprises polysaccharides. Certain compounds found in mushrooms, primarily polysaccharides, can up-regulate the immune system and may have anti-cancer properties. For example, beta-glucans such as lentinan have been shown in laboratory studies to stimulate macrophage, NK cells, T cells and immune system cytokines and have been investigated in clinical trials as immunologic adjuvants.

C. Neoantigens

In some embodiments, the additional therapy comprises neoantigen administration. Many tumors express mutations. These mutations potentially create new targetable antigens (neoantigens) for use in T cell immunotherapy. The presence of CD8+ T cells in cancer lesions, as identified using RNA sequencing data, is higher in tumors with a high mutational burden. The level of transcripts associated with cytolytic activity of natural killer cells and T cells positively correlates with mutational load in many human tumors.

D. Chemotherapies

In some embodiments, the additional therapy comprises a chemotherapy. Suitable classes of chemotherapeutic agents include (a) Alkylating Agents, such as nitrogen mustards (e.g., mechlorethamine, cylophosphamide, ifosfamide, melphalan, chlorambucil), ethylenimines and methylmelamines (e.g., hexamethylmelamine, thiotepa), alkyl sulfonates (e.g., busulfan), nitrosoureas (e.g., carmustine, lomustine, chlorozoticin, streptozocin) and triazines (e.g., dacarbazine), (b) Antimetabolites, such as folic acid analogs (e.g., methotrexate), pyrimidine analogs (e.g., 5-fluorouracil, floxuridine, cytarabine, azauridine) and purine analogs and related materials (e.g., 6-mercaptopurine, 6-thioguanine, pentostatin), (c) Natural Products, such as vinca alkaloids (e.g., vinblastine, vincristine), epipodophylotoxins (e.g., etoposide, teniposide), antibiotics (e.g., dactinomycin, daunorubicin, doxorubicin, bleomycin, plicamycin and mitoxanthrone), enzymes (e.g., L-asparaginase), and biological response modifiers (e.g., Interferon-α), and (d) Miscellaneous Agents, such as platinum coordination complexes (e.g., cisplatin, carboplatin), substituted ureas (e.g., hydroxyurea), methylhydrazine derivatives (e.g., procarbazine), and adrenocortical suppressants (e.g., taxol and mitotane). In some embodiments, cisplatin is a particularly suitable chemotherapeutic agent.

Cisplatin has been widely used to treat cancers such as, for example, metastatic testicular or ovarian carcinoma, advanced bladder cancer, head or neck cancer, cervical cancer, lung cancer or other tumors. Cisplatin is not absorbed orally and must therefore be delivered via other routes such as, for example, intravenous, subcutaneous, intratumoral or intraperitoneal injection. Cisplatin can be used alone or in combination with other agents, with efficacious doses used in clinical applications including about 15 mg/m2 to about 20 mg/m2 for 5 days every three weeks for a total of three courses being contemplated in certain embodiments. In some embodiments, the amount of cisplatin delivered to the cell and/or subject in conjunction with the construct comprising an Egr-1 promoter operably linked to a polynucleotide encoding the therapeutic polypeptide is less than the amount that would be delivered when using cisplatin alone.

Other suitable chemotherapeutic agents include antimicrotubule agents, e.g., Paclitaxel ("Taxol") and doxorubicin hydrochloride ("doxorubicin"). The combination of an Egr-1 promoter/TNFα construct delivered via an adenoviral vector and doxorubicin was determined to be effective in overcoming resistance to chemotherapy and/or TNF-α, which suggests that combination treatment with the construct and doxorubicin overcomes resistance to both doxorubicin and TNF-α.

Doxorubicin is absorbed poorly and is preferably administered intravenously. In certain embodiments, appropriate intravenous doses for an adult include about 60 mg/m2 to about 75 mg/m2 at about 21-day intervals or about 25 mg/m2 to about 30 mg/m2 on each of 2 or 3 successive days repeated at about 3 week to about 4 week intervals or about 20 mg/m2 once a week. The lowest dose should be used in elderly patients, when there is prior bone-marrow depression caused by prior chemotherapy or neoplastic marrow invasion, or when the drug is combined with other myelopoietic suppressant drugs.

Nitrogen mustards are another suitable chemotherapeutic agent useful in the methods of the disclosure. A nitrogen mustard may include, but is not limited to, mechlorethamine (HN2), cyclophosphamide and/or ifosfamide, melphalan (L-sarcolysin), and chlorambucil. Cyclophosphamide (CYTOXAN®) is available from Mead Johnson and NEO-STAR® is available from Adria), is another suitable chemotherapeutic agent. Suitable oral doses for adults include, for example, about 1 mg/kg/day to about 5 mg/kg/day, intravenous doses include, for example, initially about 40 mg/kg to about 50 mg/kg in divided doses over a period of about 2 days to about 5 days or about 10 mg/kg to about 15 mg/kg about every 7 days to about 10 days or about 3 mg/kg to about 5 mg/kg twice a week or about 1.5 mg/kg/day to about 3 mg/kg/day. Because of adverse gastrointestinal effects, the intravenous route is preferred. The drug also sometimes is administered intramuscularly, by infiltration or into body cavities.

Additional suitable chemotherapeutic agents include pyrimidine analogs, such as cytarabine (cytosine arabinoside), 5-fluorouracil (fluorouracil; 5-FU) and floxuridine (fluorode-oxyuridine; FudR). 5-FU may be administered to a subject in a dosage of anywhere between about 7.5 to about 1000 mg/m2. Further, 5-FU dosing schedules may be for a variety of time periods, for example up to six weeks, or as determined by one of ordinary skill in the art to which this disclosure pertains.

Gemcitabine diphosphate (GEMZAR®, Eli Lilly & Co., "gemcitabine"), another suitable chemotherapeutic agent, is recommended for treatment of advanced and metastatic pancreatic cancer, and will therefore be useful in the present disclosure for these cancers as well.

The amount of the chemotherapeutic agent delivered to the patient may be variable. In one suitable embodiment, the chemotherapeutic agent may be administered in an amount effective to cause arrest or regression of the cancer in a host, when the chemotherapy is administered with the construct. In other embodiments, the chemotherapeutic agent may be administered in an amount that is anywhere between 2- to 10,000-fold less than the chemotherapeutic effective dose of the chemotherapeutic agent. For example, the chemotherapeutic agent may be administered in an amount that is about 20-fold less, about 500-fold less or even about 5000-fold less than the effective dose of the chemotherapeutic agent. The chemotherapeutics of the disclosure can be tested in vivo for the desired therapeutic activity in combination with the construct, as well as for determination of effective dosages. For example, such compounds can be tested in suitable animal model systems prior to testing in humans, including, but not limited to, rats, mice, chicken, cows, monkeys, rabbits, etc. In vitro testing may also be used to determine suitable combinations and dosages, as described in the examples.

E. Radiotherapy

In some embodiments, the additional therapy or prior therapy comprises radiation, such as ionizing radiation. As used herein, "ionizing radiation" means radiation comprising particles or photons that have sufficient energy or can produce sufficient energy via nuclear interactions to produce ionization (gain or loss of electrons). An exemplary and preferred ionizing radiation is an x-radiation. Means for delivering x-radiation to a target tissue or cell are well known in the art.

In some embodiments, the amount of ionizing radiation is greater than 20 Grays (Gy) and is administered in one dose. In some embodiments, the amount of ionizing radiation is 18 Gy and is administered in three doses. In some embodiments, the amount of ionizing radiation is at least, at most, or exactly 2, 4, 6, 8, 10, 15, 16, 17, 18, 19, 20, 21, 22, 23, 24, 25, 26, 27, 18, 19, 30, 31, 32, 33, 34, 35, 36, 37, 38, 39, 40, 41, 42, 43, 44, 45, 46, 47, 48, 49, or 40 Gy (or any derivable range therein). In some embodiments, the ionizing radiation is administered in at least, at most, or exactly 1, 2, 3, 4, 5, 6, 7, 8, 9, or 10 does (or any derivable range therein). When more than one dose is administered, the does may be about 1, 4, 8, 12, or 24 hours or 1, 2, 3, 4, 5, 6, 7, or 8 days or 1, 2, 3, 4, 5, 6, 7, 8, 9, 10, 12, 14, or 16 weeks apart, or any derivable range therein.

In some embodiments, the amount of IR may be presented as a total dose of IR, which is then administered in fractionated doses. For example, in some embodiments, the total dose is 50 Gy administered in 10 fractionated doses of 5 Gy each. In some embodiments, the total dose is 50-90 Gy, administered in 20-60 fractionated doses of 2-3 Gy each. In some embodiments, the total dose of IR is at least, at most, or about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 125, 130, 135, 140, or 150 (or any derivable range therein). In some embodiments, the total dose is administered in fractionated doses of at least, at most, or exactly 1, 2, 3, 4, 5, 6, 7, 8, 9, 10, 12, 14, 15, 20, 25, 30, 35, 40, 45, or 50 Gy (or any derivable range therein. In some embodiments, at least, at most, or exactly 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 fractionated doses are administered (or any derivable range therein). In some embodiments, at least, at most, or exactly 1, 2, 3, 4, 5, 6, 7, 8, 9, 10, 11, or 12 (or any derivable range therein) fractionated doses are administered per day. In some embodiments, at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 (or any derivable range therein) fractionated doses are administered per week.

F. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

G. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IV. SAMPLE PREPARATION

In certain aspects, methods involve obtaining a sample from a subject. The methods of obtaining provided herein may include methods of biopsy such as fine needle aspiration, core needle biopsy, vacuum assisted biopsy, incisional biopsy, excisional biopsy, punch biopsy, shave biopsy or skin biopsy. In certain embodiments the sample is obtained from a biopsy from tissue by any of the biopsy methods previously mentioned. In other embodiments the sample may be obtained from any of the tissues provided herein that include but are not limited to non-cancerous or cancerous tissue and non-cancerous or cancerous tissue from the serum, gall bladder, mucosal, skin, heart, lung, breast, pancreas, blood, liver, muscle, kidney, smooth muscle, bladder, colon, intestine, brain, prostate, esophagus, or thyroid tissue. Alternatively, the sample may be obtained from any other source including but not limited to blood, sweat, hair follicle, buccal tissue, tears, menses, feces, or saliva. In certain aspects of the current methods, any medical professional such as a doctor, nurse or medical technician may obtain a biological sample for testing. Yet further, the biological sample can be obtained without the assistance of a medical professional.

A sample may include but is not limited to, tissue, cells, or biological material from cells or derived from cells of a subject. The biological sample may be a heterogeneous or homogeneous population of cells or tissues. The biological sample may be obtained using any method known to the art that can provide a sample suitable for the analytical methods described herein. The sample may be obtained by non-invasive methods including but not limited to: scraping of the skin or cervix, swabbing of the cheek, saliva collection, urine collection, feces collection, collection of menses, tears, or semen.

The sample may be obtained by methods known in the art. In certain embodiments the samples are obtained by biopsy. In other embodiments the sample is obtained by swabbing, endoscopy, scraping, phlebotomy, or any other methods known in the art. In some cases, the sample may be obtained, stored, or transported using components of a kit of the present methods. In some cases, multiple samples, such as multiple samples may be obtained for diagnosis by the methods described herein. In other cases, multiple samples, such as one or more samples from one tissue type and one or more samples from another specimen (for example serum) may be obtained for diagnosis by the methods. In some cases, multiple samples such as one or more samples from one tissue type and one or more samples from another specimen (e.g. serum) may be obtained at the same or different times. Samples may be obtained at different times are stored and/or analyzed by different methods. For example, a sample may be obtained and analyzed by routine staining methods or any other cytological analysis methods.

In some embodiments, the sample comprises a fractionated sample, such as a blood sample that has been fractionated by centrifugation or other fractionation technique. The sample may be enriched in white blood cells or red blood cells. In some embodiments, the sample may be fractionated or enriched for leukocytes or lymphocytes. In some embodiments, the sample comprises a whole blood sample.

In some embodiments the biological sample may be obtained by a physician, nurse, or other medical professional such as a medical technician, endocrinologist, cytologist, phlebotomist, radiologist, or a pulmonologist. The medical professional may indicate the appropriate test or assay to perform on the sample. In certain aspects a molecular profiling business may consult on which assays or tests are most appropriately indicated. In further aspects of the current methods, the patient or subject may obtain a biological sample for testing without the assistance of a medical professional, such as obtaining a whole blood sample, a urine sample, a fecal sample, a buccal sample, or a saliva sample.

In other cases, the sample is obtained by an invasive procedure including but not limited to: biopsy, needle aspiration, endoscopy, or phlebotomy. The method of needle aspiration may further include fine needle aspiration, core needle biopsy, vacuum assisted biopsy, or large core biopsy. In some embodiments, multiple samples may be obtained by the methods herein to ensure a sufficient amount of biological material.

General methods for obtaining biological samples are also known in the art. Publications such as Ramzy, Ibrahim Clinical Cytopathology and Aspiration Biopsy 2001, which is herein incorporated by reference in its entirety, describes general methods for biopsy and cytological methods. In one embodiment, the sample is a fine needle aspirate of a tumor or neoplasm. In some cases, the fine needle aspirate sampling procedure may be guided by the use of an ultrasound, X-ray, or other imaging device.

In some embodiments of the present methods, the molecular profiling business may obtain the biological sample from a subject directly, from a medical professional, from a third party, or from a kit provided by a molecular profiling business or a third party. In some cases, the biological sample may be obtained by the molecular profiling business after the subject, a medical professional, or a third party acquires and sends the biological sample to the molecular profiling business. In some cases, the molecular profiling business may provide suitable containers, and excipients for storage and transport of the biological sample to the molecular profiling business.

In some embodiments of the methods described herein, a medical professional need not be involved in the initial diagnosis or sample acquisition. An individual may alternatively obtain a sample through the use of an over the counter (OTC) kit. An OTC kit may contain a means for obtaining said sample as described herein, a means for storing said sample for inspection, and instructions for proper use of the kit. In some cases, molecular profiling services are included in the price for purchase of the kit. In other cases, the molecular profiling services are billed separately. A sample suitable for use by the molecular profiling business may be any material containing tissues, cells, nucleic acids, genes, gene fragments, expression products, gene expression products, or gene expression product fragments of an individual to be tested. Methods for determining sample suitability and/or adequacy are provided.

In some embodiments, the subject may be referred to a specialist such as an oncologist, surgeon, or endocrinologist. The specialist may likewise obtain a biological sample for testing or refer the individual to a testing center or laboratory for submission of the biological sample. In some cases the medical professional may refer the subject to a testing center or laboratory for submission of the biological sample. In other cases, the subject may provide the sample. In some cases, a molecular profiling business may obtain the sample.

V. ADMINISTRATION OF THERAPEUTIC COMPOSITIONS

The therapy provided herein may comprise administration of a combination of therapeutic agents, such as a first cancer therapy and a second cancer therapy. The therapies may be administered in any suitable manner known in the art. For example, the first and second cancer treatment may be administered sequentially (at different times) or concurrently (at the same time). In some embodiments, the first and second cancer treatments are administered in a separate composition. In some embodiments, the first and second cancer treatments are in the same composition.

Embodiments of the disclosure relate to compositions and methods comprising therapeutic compositions. The different therapies may be administered in one composition or in more than one composition, such as 2 compositions, 3 compositions, or 4 compositions. Various combinations of the agents may be employed.

The therapeutic agents of the disclosure may be administered by the same route of administration or by different routes of administration. In some embodiments, the cancer therapy is administered intravenously, intramuscularly, subcutaneously, topically, orally, transdermally, intraperitoneally, intraorbitally, by implantation, by inhalation, intrathecally, intraventricularly, or intranasally. In some embodiments, the antibiotic is administered intravenously, intramuscularly, subcutaneously, topically, orally, transdermally, intraperitoneally, intraorbitally, by implantation, by inhalation, intrathecally, intraventricularly, or intranasally. The appropriate dosage may be determined based on the type of disease to be treated, severity and course of the disease, the clinical condition of the individual, the individual's clinical history and response to the treatment, and the discretion of the attending physician.

The treatments may include various "unit doses." Unit dose is defined as containing a predetermined-quantity of the therapeutic composition. The quantity to be administered, and the particular route and formulation, is within the skill of determination of those in the clinical arts. A unit dose need not be administered as a single injection but may comprise continuous infusion over a set period of time. In some embodiments, a unit dose comprises a single administrable dose.

The quantity to be administered, both according to number of treatments and unit dose, depends on the treatment effect desired. An effective dose is understood to refer to an amount necessary to achieve a particular effect. In the practice in certain embodiments, it is contemplated that doses in the range from 10 mg/kg to 200 mg/kg can affect the protective capability of these agents. Thus, it is contemplated that doses include doses of about 0.1, 0.5, 1, 5, 10, 15, 20, 25, 30, 35, 40, 45, 50, 55, 60, 65, 70, 75, 80, 85, 90, 100, 105, 110, 115, 120, 125, 130, 135, 140, 145, 150, 155, 160, 165, 170, 175, 180, 185, 190, 195, and 200, 300, 400, 500, 1000 µg/kg, mg/kg, µg/day, or mg/day or any range derivable therein. Furthermore, such doses can be administered at multiple times during a day, and/or on multiple days, weeks, or months.

In certain embodiments, the effective dose of the pharmaceutical composition is one which can provide a blood level of about 1 µM to 150 µM. In another embodiment, the effective dose provides a blood level of about 4 µM to 100 µM; or about 1 µM to 100 µM; or about 1 µM to 50 µM; or about 1 µM to 40 µM; or about 1 µM to 30 µM; or about 1 µM to 20 µM; or about 1 µM to 10 µM; or about 10 µM to 150 µM; or about 10 µM to 100 µM; or about 10 µM to 50 µM; or about 25 µM to 150 µM; or about 25 µM to 100 µM; or about 25 µM to 50 µM; or about 50 µM to 150 µM; or about 50 µM to 100 µM (or any range derivable therein). In other embodiments, the dose can provide the following blood level of the agent that results from a therapeutic agent being administered to a subject: about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 µM or any range derivable therein. In certain embodiments, the therapeutic agent that is administered to a subject is metabolized in the body to a metabolized therapeutic agent, in which case the blood levels may refer to the amount of that agent. Alternatively, to the extent the therapeutic agent is not metabolized by a subject, the blood levels discussed herein may refer to the unmetabolized therapeutic agent.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance or other therapies a subject may be undergoing.

It will be understood by those skilled in the art and made aware that dosage units of µg/kg or mg/kg of body weight can be converted and expressed in comparable concentration units of µg/ml or mM (blood levels), such as 4 µM to 100 µM. It is also understood that uptake is species and organ/tissue dependent. The applicable conversion factors and physiological assumptions to be made concerning uptake and concentration measurement are well-known and would permit those of skill in the art to convert one concentration measurement to another and make reasonable comparisons and conclusions regarding the doses, efficacies and results described herein.

VI. METHODS OF TREATMENT

Provided herein are methods for treating or delaying progression of cancer in an subject through the administration of therapeutic compositions.

In some embodiments, the therapies result in a sustained response in the individual after cessation of the treatment. The methods described herein may find use in treating conditions where enhanced immunogenicity is desired such as increasing tumor immunogenicity for the treatment of cancer.

In some embodiments, the individual has cancer that is resistant (has been demonstrated to be resistant) to one or more anti-cancer therapies. In some embodiments, resistance to anti-cancer therapy includes recurrence of cancer or refractory cancer. Recurrence may refer to the reappearance of cancer, in the original site or a new site, after treatment. In some embodiments, resistance to anti-cancer therapy includes progression of the cancer during treatment with the anti-cancer therapy. In some embodiments, the cancer is at early stage or at late stage.

In some embodiments of the methods of the present disclosure, the cancer has low levels of T cell infiltration. In some embodiments, the cancer has no detectable T cell infiltrate. In some embodiments, the cancer is a non-immunogenic cancer (e.g., non-immunogenic colorectal cancer and/or ovarian cancer). Without being bound by theory, the combination treatment may increase T cell (e.g., CD4+ T cell, CD8+ T cell, memory T cell) priming, activation, proliferation, and/or infiltration relative to prior to the administration of the combination.

The cancer may be a solid tumor, metastatic cancer, or non-metastatic cancer. In certain embodiments, the cancer may originate in the bladder, blood, bone, bone marrow, brain, breast, urinary, cervix, esophagus, duodenum, small intestine, large intestine, colon, rectum, anus, gum, head, kidney, liver, lung, nasopharynx, neck, ovary, prostate, skin, stomach, testis, tongue, or uterus.

The cancer may specifically be of the following histological type, though it is not limited to these: neoplasm, malignant; carcinoma; undifferentiated, bladder, blood, bone, brain, breast, urinary, esophageal, thymomas, duodenum, colon, rectal, anal, gum, head, kidney, soft tissue, liver, lung, nasopharynx, neck, ovary, prostate, skin, stomach, testicular, tongue, uterine, thymic, cutaneous squamous-cell, noncolorectal gastrointestinal, colorectal, melanoma, Merkel-cell, renal-cell, cervical, hepatocellular, urothelial, non-small cell lung, head and neck, endometrial, esophagogastric, small-cell lung mesothelioma, ovarian, esophagogastric, glioblastoma, adrencorical, uveal, pancreatic, germ-cell, giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; bronchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; Sertoli cell carcinoma; Leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; cutaneous melanoma, blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma; hepatoblastoma; carcinosarcoma; mesenchymoma, malignant; Brenner tumor, malignant; phyllodes tumor, malignant; synovial sarcoma; malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In some embodiments, the cancer comprises cutaneous squamous-cell carcinoma, non-colorectal and colorectal gastrointestinal cancer, Merkel-cell carcinoma, anal cancer, cervical cancer, hepatocellular cancer, urothelial cancer, melanoma, lung cancer, non-small cell lung cancer, small cell lung cancer, head and neck cancer, kidney cancer, bladder cancer, Hodgkin's lymphoma, pancreatic cancer, or skin cancer.

In some embodiments, the cancer comprises lung cancer, pancreatic cancer, metastatic melanoma, kidney cancer, bladder cancer, head and neck cancer, or Hodgkin's lymphoma.

Methods may involve the determination, administration, or selection of an appropriate cancer "management regimen" and predicting the outcome of the same. As used herein the phrase "management regimen" refers to a management plan that specifies the type of examination, screening, diagnosis, surveillance, care, and treatment (such as dosage, schedule and/or duration of a treatment) provided to a subject in need thereof (e.g., a subject diagnosed with cancer).

The term "treatment" or "treating" means any treatment of a disease in a mammal, including: (i) preventing the disease, that is, causing the clinical symptoms of the disease not to develop by administration of a protective composition prior to the induction of the disease; (ii) suppressing the disease, that is, causing the clinical symptoms of the disease not to develop by administration of a protective composition after the inductive event but prior to the clinical appearance or reappearance of the disease; (iii) inhibiting the disease, that is, arresting the development of clinical symptoms by administration of a protective composition after their initial appearance; and/or (iv) relieving the disease, that is, causing the regression of clinical symptoms by administration of a protective composition after their initial appearance. In some embodiments, the treatment may exclude prevention of the disease.

In certain aspects, further cancer or metastasis examination or screening, or further diagnosis such as contrast enhanced computed tomography (CT), positron emission tomography-CT (PET-CT), and magnetic resonance imaging (MRI) may be performed for the detection of cancer or cancer metastasis in patients determined to have a certain gut microbiome composition.

VII. KITS

Certain aspects of the present invention also concern kits containing compositions of the invention or compositions to implement methods of the invention. In some embodiments, kits can be used to evaluate exosome levels and/or markers. In certain embodiments, a kit contains, contains at least or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1,000 or more probes, primers or primer sets, synthetic molecules, detection agents, antibodies or inhibitors, or any value or range and combination derivable therein. In some embodiments, there are kits for evaluating exosome level, composition, surface markers, or size in a cell.

Kits may comprise components, which may be individually packaged or placed in a container, such as a tube, bottle, vial, syringe, or other suitable container means.

Individual components may also be provided in a kit in concentrated amounts; in some embodiments, a component is provided individually in the same concentration as it would be in a solution with other components. Concentrations of components may be provided as 1×, 2×, 5×, 10×, or 20× or more.

Kits for using probes, synthetic nucleic acids, nonsynthetic nucleic acids, and/or inhibitors of the disclosure for prognostic or diagnostic applications are included as part of the disclosure. Specifically contemplated are any such molecules corresponding to any biomarker identified herein, which includes nucleic acid primers/primer sets and probes that are identical to or complementary to all or part of a biomarker, which may include noncoding sequences of the biomarker, as well as coding sequences of the biomarker.

In certain aspects, negative and/or positive control nucleic acids, probes, and inhibitors are included in some kit embodiments. In addition, a kit may include a sample that is a negative or positive control for exosome isolation, characterization, or levels.

It is contemplated that any method or composition described herein can be implemented with respect to any other method or composition described herein and that different embodiments may be combined. The claims originally filed are contemplated to cover claims that are multiply dependent on any filed claim or combination of filed claims.

Embodiments of the disclosure include kits for analysis of a pathological sample by assessing exosome profile for a sample comprising, in suitable container means, two or more exosome probes or detection agents, wherein the probes or detection agents detect one or more markers identified herein.

VIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Analysis of Peripheral Blood Exosomes

A. Isolation of Exosomes from Human Plasma.

Exosomes were purified from the plasma of patients with melanoma prior (baseline) to and on treatment with nivolumab or nivolumab+ipilimumab. The plasma was processed as previously reported (Yang, S. et al. Cancer Biol Ther 18, 158-165, doi:10.1080/15384047.2017.1281499 (2017)). Specifically: Isolation of exosomes from human plasma. Approximately 1 ml of plasma per patient sample contained in a cryovial was thawed rapidly in a 37° C. water bath. The plasma was transferred into a 1.5 ml Eppendorf tube and centrifuged at room temperature (RT) for 5 min at 800 g and 10 min at 2,000 g. The supernatant was filtered with a 0.22 μm filter (cat. #6789-1302) directly into an ultracentrifuge tube (Lot #Z80615SCA, ref. #331372). A distinct filter was used for each 500 μl of plasma filtered, and each filter was subsequently cleared with 2×1 ml phosphate buffer saline (PBS), all of which was collected into the ultracentrifuge tube. Additional PBS was added to the ultracentrifuge tube to reach 11 ml. The tubes were the ultracentrifuged at 4° C. for 15 to 16 hours at 100,000 g using a Beckman Optima XE-90 ultracentrifuge. The pellet was resuspended in 200 to 300 μl of PBS by pipetting up and down. The exosomes contained in this resuspension were stored at −80° C. until further use. (see, for example, Helmink, B. A. et al. Nature 577, 549-555, doi:10.1038/s41586-019-1922-8 (2020)).

B. Flow Cytometry Analyses of Exosomes.

The exosomes were evaluated for surface marker positivity using flow cytometry. In detail, Exosomes were thawed on ice. Concentration was determined using the NanoSight NS300 nanoparticle tracking analyzer according to the manufacturer's directions, and 15 μl of exosomes (which was equivalent to approximately $4 \times 10^9$ particles on average) were mixed with 30 μl of pre-washed anti-human CD63-coated Dynabeads® (Invitrogen, 10606D). For one sample, the Nanosight measurement was erroneous and was excluded. All samples were included in the flow cytometric analyses. Round bottom 2 ml tubes were used. All pre-wash and washes thereafter were performed using 0.22 μm filtered 0.1% Bovine Serum albumin (BSA) in PBS (0.1% BSA/

PBS) and the samples were mixed well by pipetting up and down at each wash steps. 100 µl of 0.1% BSA/PBS was added to beads+ exosomes mixture for a final volume of 145 µl (15 µl of exosomes+30 µl of Dynabeads®+100 µl of 0.1% BSA/PBS). The samples were mixed by pipetting up and down and allowed to incubate for 4 to 16 hours at RT on a benchtop rotator. 300 µl 0.1% BSA/PBS was added to the samples and the samples were placed on a magnet (1 min incubation minimum). The supernatant was discarded and the beads (and bound exosomes) were washed once with 400 µl 0.1% BSA/PBS. The beads (with bound exosomes) were resuspended in 400 µl of 0.1% BSA/PBS and subsequently split into 4 distinct round bottom 2 ml tubes, each containing 100 µl. To each of these tubes, either antibodies or isotype control were added. These include: PE/Cy7 anti-human CD20 (Biolegend, cat. #302312, clone 2H7) or isotype control PE/Cy7 mouse IgG2b (Biolegend, cat. #400326, clone MCP-11); APC/Cy7 anti-human CD27 (Biolegend, cat. #356424, clone M-T271) or isotype control APC/Cy7 mouse IgG1 (Biolegend, cat. #400128, clone MOPC-21); PE/Cy7 anti-human CD9 (Biolegend, cat. #312116, clone HI9a) or isotype control PE/Cy7 mouse IgG1 (Biolegend, cat. #400126, clone MOPC-21); and Alexa Fluor 647 anti-human CD63 (Biolegend, cat. #353016, clone H5C6) or isotype control Alexa Fluor 647 mouse IgG1 (Biolegend, cat. #400130, clone MOPC-21). For each antibodies or isotype control, 0.4 µg per tube was added to each tube. The samples were allowed to incubate at RT for 1 to 3 hours, in the dark. 300 µl 0.1% BSA/PBS was added to the samples and the samples were placed on a magnet (1 min incubation). The supernatant was discarded and the beads (and bound exosomes) were washed once with 400 µl 0.1% BSA/PBS. The beads were visible on the magnet at each step of the procedure described above. The supernatant was discarded and the beads were resuspended in 200 µl of 0.1% BSA/PBS and transferred into flow cytometry (FC) tubes for FC analysis. The FC data were captured within 24 hours of completing the staining of the beads-exosomes samples. If not read immediately after completing the staining, the FC tubes were stored at 4° C. in the dark. The data was subsequently analyzed using FlowJo. Responder vs. non-responder status was blinded until FC data capture and FlowJo analyses were completed. (see, for example, Helmink, B. A. et al. Nature 577, 549-555, doi:10.1038/s41586-019-1922-8 (2020)).

Figure 7:
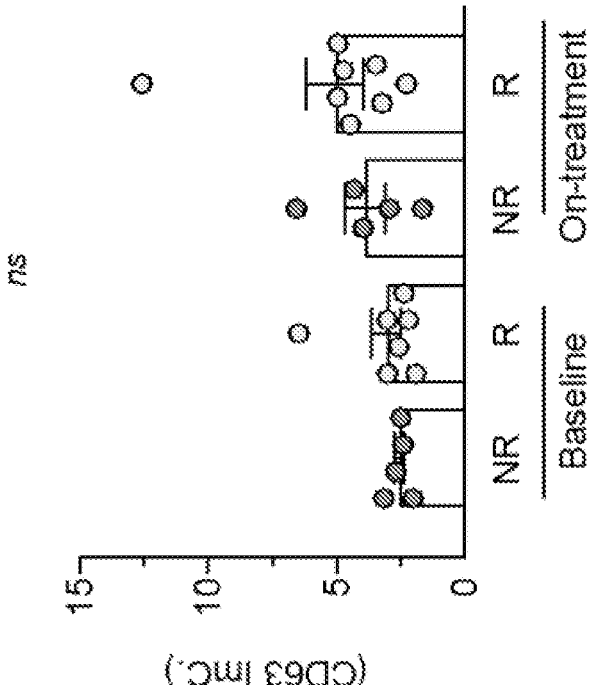
FIG. 7. Exosomes immunocapture (ImC.) with anti-CD63; FC with PE/Cy7-anti-CD9: Normalized MFI (MFI$^{CD9}$/MFI$^{Isotype}$). Graphed data for the MFI (mean fluorescence intensity) of CD9+ beads for each patient sample analyzed. BL, baseline; OT, on treatment; NR, non-responder; R: responder. The MFI CD9+ beads in similar in all samples studied. ns: not significant. CD9 is another exosomes markers.

Evidence for the successful immunocapture of CD63+ exosomes on Dynabeads with anti-CD63 antibodies is shown in FIGS. 2-6. CD9 positivity (exosomes marker) is also noted on for the CD63+ exosomes on Dynabeads (FIG. 7), supporting capture of exosomes on the Dynabeads.

C. Nanoimager Analyses.

The immunocapture of CD63+ exosomes on Dynabeads was further exemplified by nanoimaging of the beads. Specifically, Beads with exosomes stained for FC analysis for CD63 (Alexa Fluor 647 anti-human CD63) or isotype control described above (Flow cytometry analyses of exosomes) were evaluated by using the on the Nanoimager S Mark I from ONI (Oxford Nanoimaging) with the lasers 405 nm/150 mW, 488 nm/200 mW, 561 nm/300 mW, 640 nm/1 W and dual emission channels split at 560 nm. Data was processed on NimOS (Version [1.25]) from ONI. Briefly, 25 µl of sample was spotted onto a slide (Fisher Scientific, 12-550-15), covered with a 1.5H coverslip (Zeiss, 474030-9000), and immediately placed on the stage. All images were captured using HILO mode (highly inclined and laminated optical sheet) at an illumination angle of 35.0 degrees with a 10.0 ms exposure setting for 200 frames. To minimize photobleaching, the focal plane of the beads was found under the 405 nm laser at 37% power, then switched to the 640 nm laser at 25% power for image acquisition. (see, for example, Helmink, B. A. et al. Nature 577, 549-555, doi: 10.1038/s41586-019-1922-8 (2020)) FIG. 8A-C shows representative images of the nanoimaging results.

Figures 8C, 9:
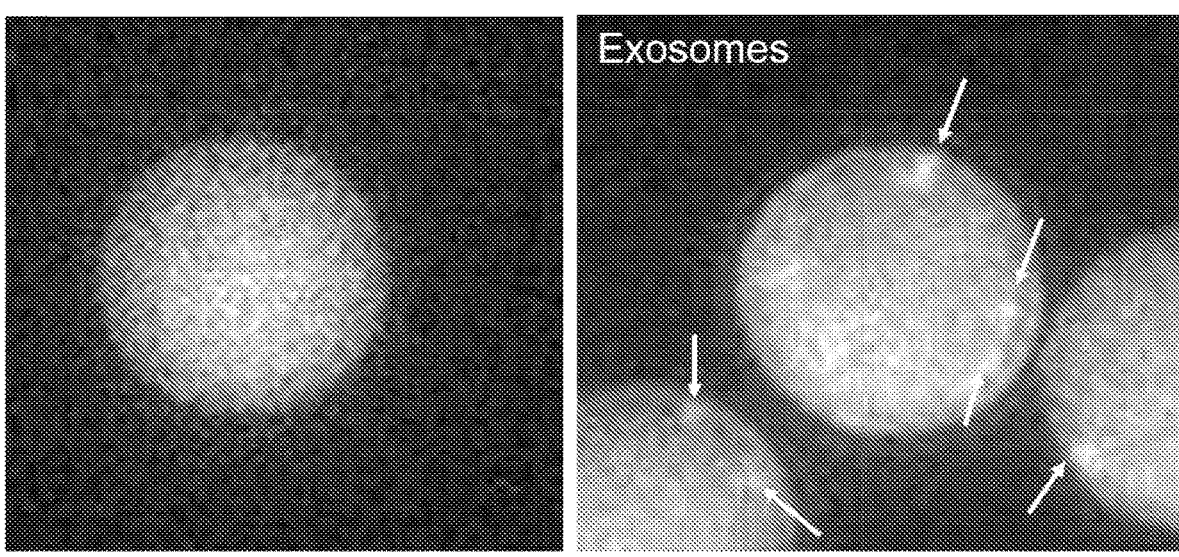
Figure 10:
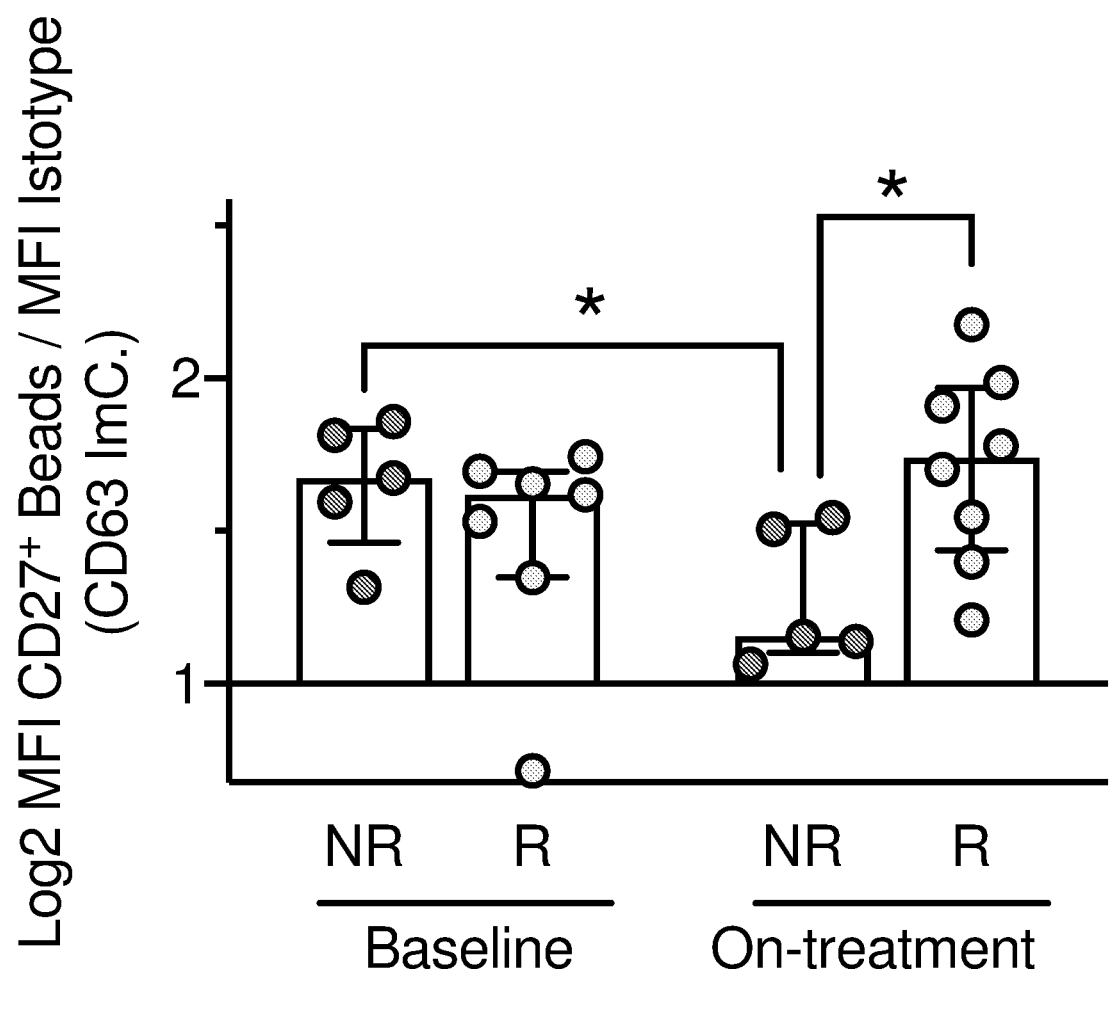
FIG. 10. Exosomes immunocapture (ImC.) with anti-CD63; FC with APC/Cy7-anti-CD27: Normalized MFI (MFI$^{CD27}$/MFI$^{Isotype}$). Graphed data for the Log 2 MFI (mean fluorescence intensity) of CD27+ of beads with immunocapture of CD63+ exosomes for each patient sample analyzed. BL, baseline; OT, on treatment; NR, non-responder; R: responder. The MFI CD27+ beads in greater in responders on-treatment.

The data obtained from immunolabeling CD63+, Dynabead captured exosomes for CD27 and CD20 is shown in FIGS. 9-10. The data indicate an increased abundance of CD20+ and CD27+ exosomes (captured with anti-CD63 Dynabeads) in the plasma of patients categorized as "responding" (R) to the treatment (see above) compared to those that did not respond (NR) at on-treatment timepoints.

Using the methods described above, it was found that there was an increased abundance of B-cell related exosomes (CD20+ exosome-coated beads) in the peripheral blood of responders versus non-responders at early on-treatment time-points (FIG. 1). FIGS. 2-10 further exemplify embodiments of the disclosure.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of treating skin cancer in a subject comprising administering to the subject immune checkpoint blockade (ICB) therapy comprising nivolumab and ipilimumab after CD20-expressing B-cell exosomes have been detected in a biological sample from the subject.

2. The method of claim 1, wherein the subject has been determined to have an increase in the amount of CD20-expressing B-cell exosomes in comparison to a control, wherein the control represents an amount of CD20-expressing B-cell exosomes in a biological sample from a subject that has been determined to not respond effectively to ICB therapy.

3. The method of claim 1, wherein the subject has been determined to have an amount of CD20-expressing B-cell exosomes that is not significantly different or is more than a control amount, wherein the control represents an amount of CD20-expressing B-cell exosomes in a biological sample from a subject that has been determined to respond effectively to ICB therapy.

4. The method of claim 1, wherein the method further comprises administering at least one additional anticancer treatment.

5. The method of claim 4, wherein the at least one additional anticancer treatment is surgical therapy, chemotherapy, radiation therapy, hormonal therapy, immunotherapy, small molecule therapy, receptor kinase inhibitor therapy, anti-angiogenic therapy, cytokine therapy, cryotherapy or a biological therapy.

6. The method of claim 1, wherein the ICB therapy further comprises one or more of pembrolizumab, pidilizumab, or tremelimumab.

7. The method of claim 1, wherein the B-cell exosomes are further defined as positive for one or more of CD63, CD9, CD27, and/or GPC1.

8. The method of claim 1, wherein the B-cell exosomes were detected by an immunocapture assay.

9. The method of claim 1, wherein CD63+ exosomes were detected in a biological sample.

10. The method of claim 1, wherein the biological sample comprises a blood sample, a serum sample, a plasma sample, or a fraction of a blood, serum, or plasma sample.

11. The method of claim 10, wherein the biological sample comprises a serum sample.

12. The method of claim 1, wherein the biological sample comprises a sample that has been filtered through a 0.1-0.3 μm filter.

13. The method of claim 1, wherein the biological sample comprises a sample that has undergone ultracentrifugation.

14. The method of claim 1, wherein the biological sample comprises a sample that has undergone FACS analysis or an immunoanalysis to detect markers.

15. A method for predicting a response to ICB therapy in a subject having skin cancer, the method comprising:
(a) obtaining a biological sample from the subject;
(b) detecting the amount of CD20-expressing B-cell exosomes in the sample from the subject;
(c) comparing the amount of CD20-expressing B-cell exosomes in the sample from the subject to a control subject that has been determined to not respond effectively to ICB therapy;
(d) identifying the subject as likely to respond to the ICB therapy when the detected amount of CD20-expressing B-cell exosomes in the subject sample is increased compared to the control subject sample; and
(e) administering ICB therapy to the subject if the subject is identified as likely to respond to the ICB therapy,
wherein the ICB therapy comprises nivolumab and ipilimumab.

16. A method of detecting CD20-expressing B-cell exosomes in a subject with skin cancer, the method comprising:
(a) obtaining a sample from the subject; and
(b) detecting whether CD20-expressing B-cell exosomes are present in the sample by contacting the sample with a labeled anti-human CD20 antibody, and detecting binding between CD20-expressing B-cell exosomes and the antibody,
wherein the subject is determined to have an increase in the amount of detected CD20-expressing B-cell exosomes in comparison to a control representing an amount of CD20-expressing B-cell exosomes in a sample from a subject that has been determined to not respond effectively to ICB therapy, or
wherein the subject has been determined to have an amount of detected CD20-expressing B-cell exosomes that is not significantly different from or is more than a control representing an amount of CD20-expressing B-cell exosomes in a sample from a subject that has been determined to respond effectively to ICB therapy,
wherein the ICB therapy comprises nivolumab and ipilimumab.

\* \* \* \* \*